(12) United States Patent
Kraus et al.

(10) Patent No.: US 10,945,994 B2
(45) Date of Patent: Mar. 16, 2021

(54) COMBINATIONS COMPRISING A PYRROLIDINE-2,5-DIONE IDO1 INHIBITOR AND AN ANTI-BODY

(71) Applicants: Pfizer Inc., New York, NY (US); iTeos Therapeutics, Charleroi (BE)

(72) Inventors: Manfred Kraus, San Diego, CA (US); Sandra Cauwenberghs, Charleroi (BE); Stefano Crosignani, Nivelles (BE); Gregory Driessens, Charleroi (BE)

(73) Assignees: Pfizer Inc., New York, NY (US); iTEOS THERAPEUTICS, Charleroi (BE)

( * ) Notice: Subject to any disclaimer, the term of this patent is extended or adjusted under 35 U.S.C. 154(b) by 168 days.

(21) Appl. No.: 15/573,190

(22) PCT Filed: May 12, 2016

(86) PCT No.: PCT/IB2016/052748
§ 371 (c)(1),
(2) Date: Nov. 10, 2017

(87) PCT Pub. No.: WO2016/181348
PCT Pub. Date: Nov. 17, 2016

(65) Prior Publication Data
US 2018/0125817 A1 May 10, 2018

Related U.S. Application Data

(60) Provisional application No. 62/321,122, filed on Apr. 11, 2016, provisional application No. 62/161,654, filed on May 14, 2015.

(51) Int. Cl.
*A61K 31/404* (2006.01)
*A61K 39/395* (2006.01)
(Continued)

(52) U.S. Cl.
CPC .......... *A61K 31/404* (2013.01); *A61K 31/337* (2013.01); *A61K 31/495* (2013.01);
(Continued)

(58) Field of Classification Search
CPC ...... A61K 31/404; A61K 39/395; A61P 35/00
See application file for complete search history.

(56) References Cited

U.S. PATENT DOCUMENTS 9,603,836 B2 * 3/2017 Crosignani .............. A61P 35/00
9,949,951 B2 * 4/2018 Crosignani .......... C07D 403/04
(Continued)

FOREIGN PATENT DOCUMENTS

WO  WO 2005/058035 A1   6/2005
WO  WO 2007/124252 A2   11/2007
(Continued)

OTHER PUBLICATIONS

Spranger et al. (Journal for ImmunoTherapy of Cancer, 2014, 2:3, pp. 1-14) (Year: 2014).*
(Continued)

*Primary Examiner* — Theodore R. Howell
(74) *Attorney, Agent, or Firm* — Howson and Howson LLP; Cathy Kodroff

(57) ABSTRACT

Combinations of an IDO1 inhibitor (e.g., a 3-(5-fluoro-1H-indol-3-yl)pyrrolidine-2,5-dione compound), with an anti-PD1 antibody or anti-PD-L1 antibody, and an anti-4-1BB antibody, as selected anti-cancer or anti-viral agents are provided. Also provided are use of these combinations for the treatment and/or prevention of cancer and endometriosis.

26 Claims, 16 Drawing Sheets

Specification includes a Sequence Listing.

4-1BB + PD-L1 vs. 4-1BB + PD-L1 + PF-06840003

(51) Int. Cl.
| | |
|---|---|
| *A61P 35/00* | (2006.01) |
| *A61K 45/06* | (2006.01) |
| *A61K 31/519* | (2006.01) |
| *A61K 31/53* | (2006.01) |
| *A61K 31/495* | (2006.01) |
| *A61P 31/12* | (2006.01) |
| *A61P 15/00* | (2006.01) |
| *A61K 31/337* | (2006.01) |
| *C07K 16/28* | (2006.01) |
| *A61K 9/00* | (2006.01) |
| *A61K 39/00* | (2006.01) |

(52) U.S. Cl.
CPC ............ *A61K 31/519* (2013.01); *A61K 31/53* (2013.01); *A61K 39/395* (2013.01); *A61K 39/39558* (2013.01); *A61K 45/06* (2013.01); *A61P 15/00* (2018.01); *A61P 31/12* (2018.01); *A61P 35/00* (2018.01); *C07K 16/2818* (2013.01); *A61K 9/0019* (2013.01); *A61K 9/0053* (2013.01); *A61K 2039/505* (2013.01); *A61K 2300/00* (2013.01)

(56) References Cited

U.S. PATENT DOCUMENTS

| | | | |
|---|---|---|---|
| 10,398,679 B2 * | 9/2019 | Crosignani | ........ A61K 31/4015 |
| 2013/0034559 A1 | 2/2013 | Queva et al. | |
| 2015/0133422 A1 | 5/2015 | Crosignani et al. | |
| 2015/0225367 A1 | 8/2015 | Crosignani et al. | |
| 2015/0266857 A1 | 9/2015 | Crosignani et al. | |
| 2015/0329525 A1 | 11/2015 | Crosignani et al. | |
| 2017/0267753 A1 * | 9/2017 | Ehrenpreis | ............. A61K 45/06 |

FOREIGN PATENT DOCUMENTS

| | | |
|---|---|---|
| WO | WO 2008/068621 A2 | 6/2008 |
| WO | WO 2011/066389 A1 | 6/2011 |
| WO | WO 2013/079174 A1 | 6/2013 |
| WO | WO 2013/079197 A1 | 6/2013 |
| WO | WO 2015/173764 A1 | 11/2015 |

OTHER PUBLICATIONS

Chen et al. (Cancer Immunology Research, 3(2), 149-160, Nov. 11, 2014). (Year: 2014).*

Godin-Ethier et al., "Indoleamine 2,3-dioxygenase expression in human cancers: clinical and immunologic perspectives", Clin Cancer Res, vol. 17(22):6985-6991, Nov. 2011.

Holmgaard et al., "Indoleamine 2,3-dioxygenase is a critical resistance mechanism in antitumor T cell immunotherapy targeting CTLA-4", J Exp Med, vol. 210(7):1389-1402, Jul. 2013.

Munn et al., "Blocking IDO activity to enhance anti-tumor immunity", Front Biosci, Voll. 4:734-45, Jan. 2012.

Munn et al., "Indoleamine 2,3 dioxygenase and metabolic control of immune responses", Trends Immunol, vol. 34(3):137-43, Mar. 2013.

Uyttenhove et al., "Evidence for a tumoral immune resistance mechanism based on tryptophan degradation by indoleamine 2,3-dioxygenase", Nat Med, vol. 9(10):1269-1274, Oct. 2003.

U.S. Appl. No. 62/231,122, filed Apr. 13, 2016.

U.S. Appl. No. 62/161,654, filed May 14, 2015.

International Search Report, dated Jul. 12, 2016, issued on related International Patent Application No. PCT/IB2016/052748.

Van der Meer et al., "Automated separation of whole blood in top and bottom bags into components using the Compomat G4", Vox Sang, vol. 76(2):90-99, Mar. 1999.

Rohrig et al., "Rational design of 4-aryl-1,2,3-triazoles for indoleamine 2,3-dioxygenase 1 inhibition", J Med Chem, vol. 55(11):5270-5290, Jun. 2012.

Sono et al., "Enzyme kinetic and spectroscopic studies of inhibitor and effector interactions with indoleamine 2,3-dioxygenase. 1. Norharman and 4-phenylimidazole binding to the enzyme as inhibitors and heme ligands", Biochemistry, vol. 29(13): 5392-5399, Jun. 1989.

Stites et al. (eds), Basic and Clinical Immunology (8th Edition), Appleton & Lange: Norwalk, CT, p. 71 and Chapter 6, Jan. 1994.

Johnson et al., "Host indoleamine 2,3-dioxygenase: contribution to systemic acquired tumor tolerance", Immunol Invest, vol. 41(6-7):765-797, Sep. 2012.

* cited by examiner

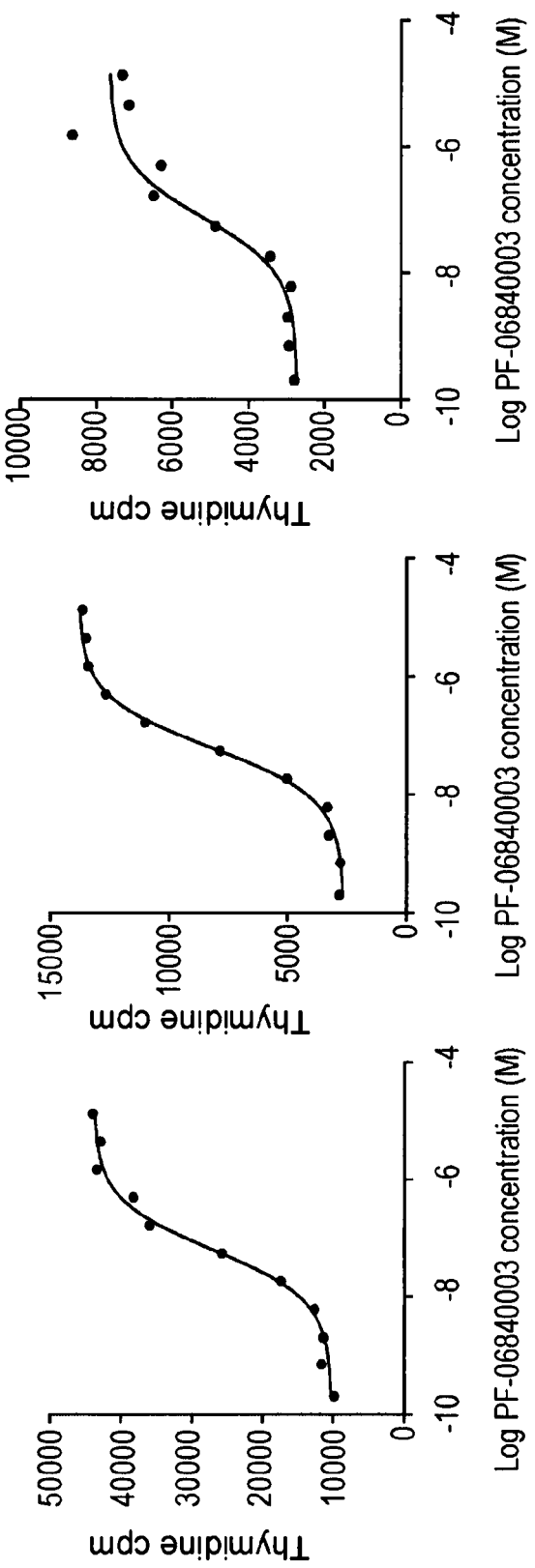

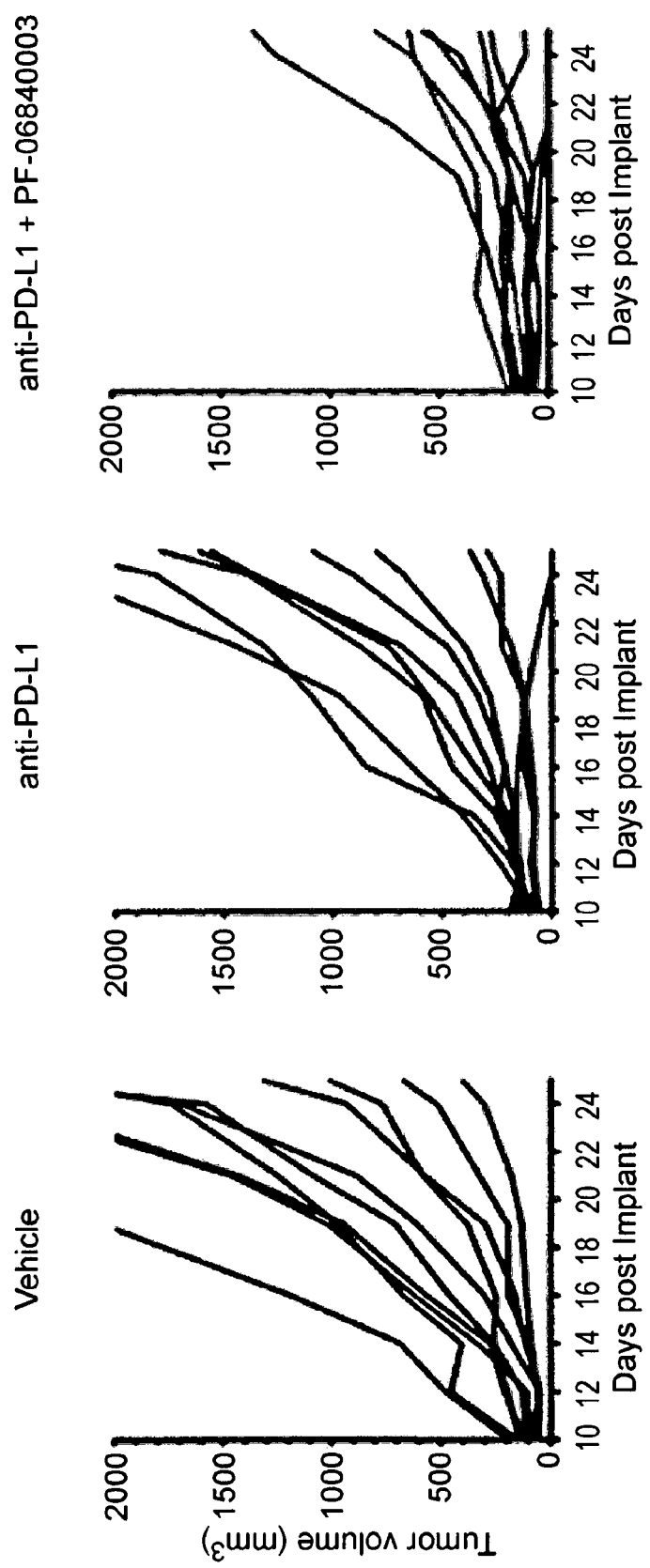

4-1BB vs. 4-1BB + PF-06840003

4-1BB + PD-L1 vs. 4-1BB + PD-L1 + PF-06840003

COMBINATIONS COMPRISING A PYRROLIDINE-2,5-DIONE IDO1 INHIBITOR AND AN ANTI-BODY

FIELD OF INVENTION

The present invention relates to combination therapies utilizing inhibitors of IDO1 (indoleamine 2,3-dioxygenase 1).

BACKGROUND OF INVENTION

Indoleamine 2,3-dioxygenase 1 (IDO1) is an intracellular monomeric, heme-containing enzyme that catalyzes the first and rate limiting step of L-tryptophan (Trp) catabolism along the kynurenine pathway, leading to the production of N-formylkynurenine. 95% of Trp is metabolized through this kynurenine pathway. The kynurenine pathway (KYN) initiates the production of neuroactive and immunoregulatory metabolites, collectively known as kynurenines and provides precursors that supplement dietary niacin for the biosynthesis of NAD+ and NADP+.

By locally depleting tryptophan and increasing kynurenines, IDO1 expressed by antigen presenting cells (APCs) such as dendritic cells (plasmacystoid DCs in tumor draining lymph nodes) can greatly affect T-cell proliferation and survival and activate regulatory T cells thereby reducing proinflammatory responses. IDO1 can thus provide "immune privilege" to tissues subject to chronic inflammations such as infectious and allergic diseases, transplantation and cancer. Because such tolerogenic responses can be expected to operate in a variety of physiopathological conditions, tryptophan metabolism and kynurenine production through IDO1 might represent a crucial interface between the immune and nervous system. Expression of IDO1 is upregulated by proinflammatory cytokines and can be detected in a variety of tissues, including placenta, spleen, thymus, lung, digestive tract, and central nervous system (reviewed in Munn et al. Trends Immunol, 2013, 34, 137-43).

IDO1 has emerged as a promising molecular target of new therapeutic agents for treating cancer as well as other diseases characterized by the reduction of local Trp levels and/or to imbalances in the level of cytotoxic metabolites produced by the kynurenine pathway (reviewed in Munn et al. Trends Immunol, 2013, 34, 137-43). Indeed inhibition of IDO1 activity as a therapeutic strategy has been tested in preclinical models of many diseases, with the most widely used IDO1 inhibitor, the tryptophan analogue L-1-methyl-tryptophan (L-1MT). Treatment with L-1MT, alone or in combination with other agents, attenuated disease severity in animal models of arthritis, ischemia-reperfusion injury, endotoxin shock, human immunodeficiency virus (HIV)/simian immunodeficiency virus (SIV) infection, airway inflammation, and cancer (Uyttenhove et al., Nat Med, 2003, 9, 10, 1269-1274; Holmgaard et al., J Exp Med, 2013, 210, 7, 1389-1402), among others. For cancer, IDO1 induction has been observed in vivo during rejection of allogeneic tumors, indicating a possible role for this enzyme in the tumor rejection process (Uyttenhove et al., Nat Med, 2003, 9, 10, 1269-1274; Holmgaard et al., J Exp Med, 2013, 210, 7, 1389-1402). Cervical carcinoma cells (or HeLa cells) co-cultured with peripheral blood lymphocytes (PBLs) acquire an immuno-inhibitory phenotype through up-regulation of IDO1 activity. A reduction in PBL proliferation upon treatment with interleukin-2 (IL2) was believed to result from IDO1 released by the tumor cells in response to gamma interferon (IFN)-g (γ) secretion by the PBLs. IDO1 activity in tumor cells may thus serve to impair anti-tumor responses, a process in which IFNg plays a central role. Further evidence for a tumoral immune resistance mechanism based on tryptophan degradation by IDO1 comes from the observation that most human tumors constitutively express IDO1, and that expression of IDO1 by immunogenic mouse tumor cells prevents their rejection (reviewed in Munn et al., Front Biosci, 2012, 4, 734-45; Godin-Ethier et al. Clin Cancer Res 2011, 17, 6985-6991; Johnson et al. Immunol Invest 2012, 41, 6-7, 765-797). This effect is accompanied by a lack of accumulation of specific T cells at the tumor site and can be partly reverted by systemic treatment of mice with an inhibitor of IDO1, in the absence of noticeable toxicity (Holmgaard et al., J Exp Med, 2013, 210, 7, 1389-1402).

IDO1 expression has been demonstrated by immunohistochemistry in a wide spectrum of cancer patients. IDO1 mRNA, protein or modification of the ratio of tryptophan and kynurenine in the blood have been detected in patients with malignant melanoma, acute myelogenous leukemia, pancreatic, colorectal, prostate, cervical, brain, endometrial and ovarian cancers amongst others. In several malignancies, the presence of IDO1 is an independent predictor of a worse clinical outcome (reviewed in Munn et al., Front Biosci, 2012, 4, 734-45).

Therefore, there is a need for new therapeutic regimens for cancer treatment and/or prevention.

SUMMARY OF THE INVENTION

The regimens and compositions herein help meet the current need for regimens in a patient diagnosed with cancer, or any subject at risk of developing a cancer.

In one aspect, a combination comprises (a) a 3-(5-fluoro-1H-indol-3-yl)pyrrolidine-2,5-dione; and (b) at least a second active drug which is an anti-PD-1 or anti-PD-L1 antibody, e.g., avelumab. Optionally, the combination may include an additional immunomodulatory agent selected from anti-CTLA4 antibody, an anti-OX-40 antibody, an anti-4-1BB antibody, an anti-cancer antigen vaccine, an P-cadherin LP-Dual-Affinity Re-Targeting protein, a TDO inhibitor or an antibody-drug conjugate (ADC).

In one embodiment, a further immunomodulatory agent is an anti-CTLA4 antibody, e.g., ipilimumab or tremelimumab. In another embodiment, the second active drug is an anti-PD-L1 antibody such as avelumab. In another aspect, the third active agent is a p53 cancer vaccine.

In still a further embodiment, a combination regimen is provided which comprises (a) a 3-(5-fluoro-1H-indol-3-yl)pyrrolididine-2,5-dione, (b) avelumab, and optionally (c) third active drug which is a signal modulating inhibitor selected from a Pi3K/mTOR inhibitor, a Pi3K-alpha selective inhibitor, a MEK inhibitor, an enhancer of zeste homolog 2 (EZH2) inhibitor, an epidermal growth factor receptor (EGFR) inhibitor, a vascular endothelial growth factor (VEGF) inhibitor, or a selective inhibitor of the cyclin-dependent kinases CDK4 and CDK6. In a further embodiment, the third agent is the selective inhibitor of the cyclin-dependent kinases CDK4 and CDK6, e.g., palbociclib.

In still a further embodiment, the third agent is an alk/rosi inhibitor, e.g., crizotinib (Xalkori), ceritiib (Zykadia), alectinib (Chugai), or lorlatinib (Pfizer).

In yet another embodiment, a combination regimen is provided which comprises (a) a 3-(5-fluoro-1H-indol-3-yl) pyrrolididine-2,5-dione, (b) an anti-PD-1 or an anti-PD-L1 antibody (e.g., avelumab), and optionally (c) a third active drug which is ibrutinib or a chemotherapeutic. In one embodiment, the chemotherapeutic is selected from an alkylating agent, e.g., temozolomide or a tubulin-targeting agent, docetaxel.

In another aspect, a combination comprises as the 3-(5-fluoro-1H-indol-3-yl)pyrrolididine-2,5-dione, the racemate, (−)-(R)-3-(5-fluoro-1H-indol-3-yl)pyrrolidine-2,5-dione, (S)-3-(5-fluoro-1H-indol-3-yl)pyrrolidine-2,5-dione, or a mixture thereof, in combination with an anti-PD-1 or an anti-PD-L1 antibody (e.g., avelumab). Optionally, one or more of these compounds has a deuterium atom substituted for a hydrogen atom therein, i.e., is optionally deuterated, e.g., at its chiral center.

In another embodiment, a combination comprising a compound of Formula II' and/or Formula II" is provided. The composition may contain a racemic compound. Alternatively, the composition may contain a mixture of a compounds of Formula II' and Formula II", which are produced separately. Such compounds may contain a 1:1 ratio of Formula II' to Formula II", as is present in the racemate, or the R-enantiomer may be present in an amount of greater than 50%. In another alternative, a composition may contain more than 50% of the S-enantiomer. Optionally, the racemate, or one or both of the enantiomers, may be deuterated, e.g., at the chiral carbon.

Other aspects and advantages of the invention will be apparent from the following detailed description of the invention.

BRIEF DESCRIPTION OF THE DRAWINGS

FIG. 5A shows tumor growth inhibition in mice receiving Compound 1 (second line), a human anti-PD-L1 antibody (avelumab; second from bottom), or a combination thereof (bottom line), as compared to vehicle (top line), n=10 per group, randomization and treatment start on day 9 after tumor implant. FIGS. 5B-5E show the individual tumor growth curves. These results show that therapy of Avelumab and racemic 3-(5-fluoro-1H-indol -3-yl)pyrrolidine-2,5-dione is enhanced with the combination of these 2 agents.

FIG. 6 illustrates IDO Activity as a potential resistance mechanism to anti-PD-L1 treatment.

FIGS. 7A-7F shows that IDO1 inhibitor racemic 3-(5-fluoro-1H-indol-3-yl)pyrrolidine-2,5-dione rescues T cell proliferation in a T cell—SKOV3 co-culture assay. Irradiated IDO1-expressing SKOV3 cells were co-cultured with human PBMC at a ratio of 1:1 in the presence of CD3/CD28 beads and increasing concentrations of the racemate. Three different concentrations of human serum (10%, 25% or 50%) were used to mimic the consequences of protein binding in human. FIG. 7A shows proliferation of PBL in 10% HS. FIG. 7B shows proliferation of PBL in 25% HS. FIG. 7C shows proliferation of PBL in 50% HS. T cell proliferation was measured by incorporation of $^3$H-thymidine after 48 h of co-culture. IC$_{50}$ of T cell proliferation, tryptophan (Trp) decrease and kynurenine (Kyn) increase were determined. FIG. 7D illustrates Trp to Kyn conversion in 10% HS. FIG. 7E illustrates Trp to Kyn conversion in 25% HS. FIG. 7F illustrates Trp to Kyn conversion in 50% HS. Tryptophan and kynurenine concentrations in supernatant were assessed using LC-MS/MS after 24 h of co-culture.

FIGS. 8A-8E show that IDO inhibition with racemic 3-(5-fluoro-1H-indol-3-yl)pyrrolidine-2,5-dione in combination with anti-PD-L1 treatment in a CT26-implanted mouse tumor model has a significant tumor growth inhibition benefit. For in vivo experiments, 5×10$^5$ CT26 cells were resuspended in supplemented-free RPMI and injected s.c. (100 µl) using insulin syringes. Mice were randomized and treatment was started when the tumor had an average of 100 to 120 mm$^3$+/−50 mm$^3$. Antibody treatment consisted in 3 i.p. injection with 200 µg anti-mouse PDL1 separated by 3 days. IDO1 inhibitor (Compound 1) was resuspended and sonicated in Methocel vehicle (Colorcon) and mice were treated twice daily (BID) by oral gavage in the morning and evening (100 ul) until the end of the model. The anti-PD-L1 antibody clone was 10F.9G2. FIG. 8B shows the dose and treatment schedule. FIG. 8C is showing the individual tumor growth curves of the control group (vehicle treated mice). FIG. 8D shows anti-PD-L1 treated mice. FIG. 8E shows the effects of combined treatment with racemic 3-(5-fluoro-1H-indol-3-yl)pyrrolidine-2,5-dione and the anti-PD-L1 therapy.

FIG. 11A shows the percent survival for animals treated with 4-1BB, the IDO1 inhibitor, or the combination of the two active components. FIG. 11B illustrates the percent survival for animals treated with the IDO1 inhibitor alone, the two-component combination of 4-1BB and anti-PD-L1, or the three-way combination of 4-1BB, anti-PD-L1 antibody, and the IDO1 inhibitor.

DETAILED DESCRIPTION OF THE INVENTION

Combinations

Figure 1:
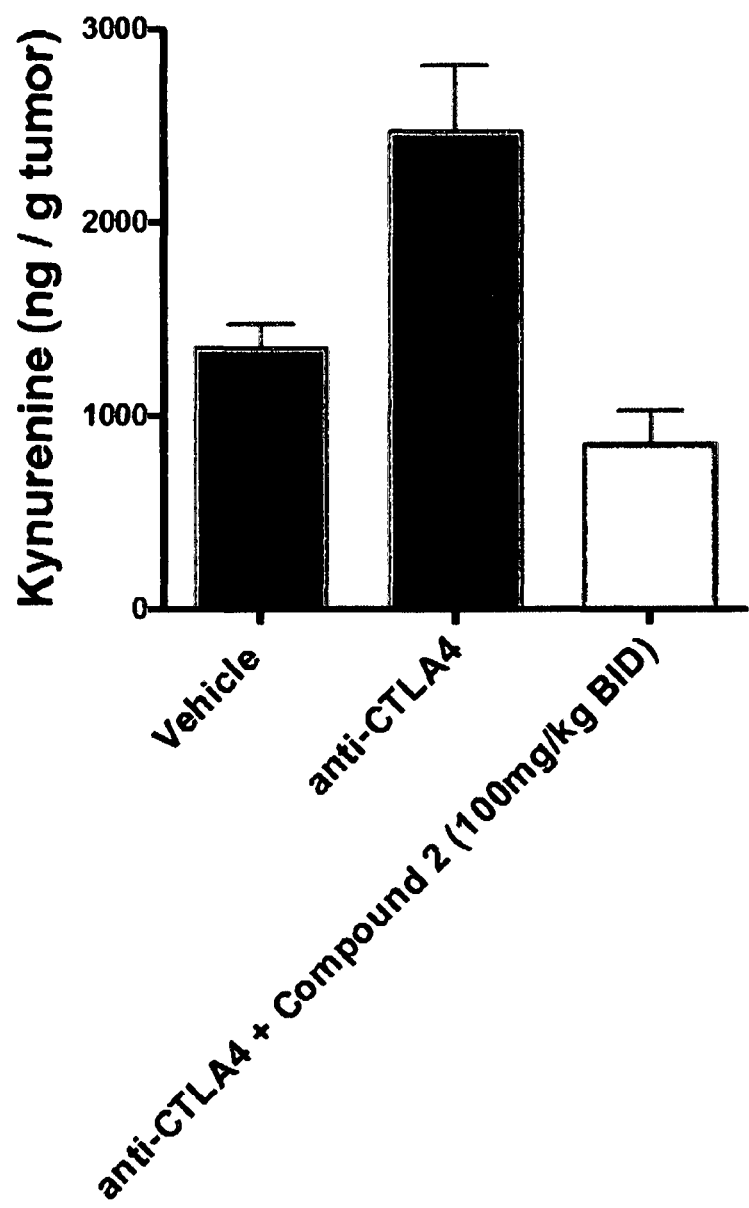
FIG. 1 is a graph showing the concentration of Kynurenine within syngeneic CT26 tumors in mice after treatment with a combination of compound 2 and an anti-CTLA4 antibody or with the single agents and a vehicle control.

Combinations comprising at least one 3-(5-fluoro-1H-indol-3-yl)pyrrolidine-2,5-dione compound and an anti-PD-1 or anti-PD-L1 antibody are provided. Optionally, the combination may contain at least a third active component, which may be a different IDO inhibitor or may another primary function and have some minor IDO inhibitory functions. For example, such combinations may include the IDO inhibitors described in US Patent Publication No. 2015/0329525A1, which claims the benefit of U.S. Provisional Patent Application No. 61/996,976, filed May 15, 2014 or its corresponding PCT application to filed on May 14, 2015 (now published as WO2015/173764), both entitled, pyrrolidine-2,5-dione derivatives, pharmaceutical compositions and methods for use as IDO1 inhibitor. In one embodiment, one or more of these IDO inhibitors may be used in a combination described herein containing an anti-PD-1 or anti-PD-L1 antibody, optionally with at least one further different active component. Optionally, more than one different IDO inhibitor may be included in the combination with an anti-PD-1 or anti-PD-L1 antibody. More preferably, the combination contains a single IDO inhibitor, an anti-PD-1 or anti-PD-L1 antibody and optionally a further active component from a different class of active drugs, which has a different mode of action. Typically, in such combination therapies, the first active component which is at least one 3-(5-fluoro-1H-indol-3-yl)pyrrolidine-2,5-dione compound and the anti-PD-1 or anti-PD-L1 antibody are formulated into separate pharmaceutical compositions or medicaments. When separately formulated, the at least two active components can be administered simultaneously or sequentially, optionally via different routes. Optionally, the treatment regimens for each of the active components in the combination have different but overlapping delivery regimens, e.g., daily, twice daily, vs. a single administration, or weekly. The second active component (anti-PD-L1 antibody) may be delivered prior to, substantially simultaneously with, or after, the at least one 3-(5-fluoro-1H-indol-3-yl)pyrrolidine-2,5-dione compound.

Also provided herein are formulations containing a single or more multiple active components useful in a combination therapy, and therapeutic and/or prophylactic regimens for treatment of cancer, endometriosis or viral infections.

The terms "combination therapy" or "combined treatment" or "in combination" as used herein denotes any form of concurrent or parallel treatment with at least two distinct therapeutic agents. Contemplated with the scope of the combinations described herein, are combinations which further include at minimum of the at least one 3-(5-fluoro-1H-indol -3-yl)pyrrolidine-2,5-dione compound and an anti-PD-1 or anti-PD-L1 antibody as the second active component. Optionally, three or more components may be used in a combination regimen. Additionally, the combinations provided herein may be used in conjunction with other types of treatment. For example, other anti-cancer treatment may be selected from the group consisting of chemotherapy, surgery, radiotherapy (radiation), and/or hormone therapy, amongst other treatments associated with the current standard of care for the patient. Similarly, for anti-viral treatments, other anti-viral agents or other treatments.

Compounds

In one embodiment, a combination as provided herein contains at least one 3-(5-fluoro -1H-indol-3-yl)pyrrolidine-2,5-dione compound in combination with an anti-PD-1 or anti-PD-L1 antibody. In one embodiment, the anti-PD-L1 antibody is avelumab.

As used herein, the term "a 3-(5-fluoro-1H-indol-3-yl)pyrrolidine-2,5-dione" refers to the racemic compound having the structure:

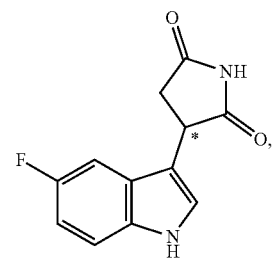

II or a enantiomer thereof, a pharmaceutically acceptable salt or solvent thereof, any of which is optionally deuterated. In one embodiment, the compound is a free base, i.e., is in neither salt nor solvate form.

The 3-(5-fluoro-1H-indol-3-yl)pyrrolidine-2,5-dione compound may be a racemate, wherein each stereoisomer is present an amount of about 50 mol % (48% to 52%). Alternatively or additionally, a separate enantiomer of the compound is used in a pharmaceutical composition.

In one embodiment, the (R)-3-(5-fluoro-1H-indol-3-yl)pyrrolidine-2,5-dione enantiomer is characterized by structure of Formula II':

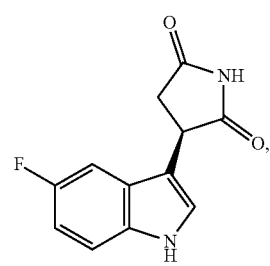

II' which is present in free base (not salt) form. Optionally, the compound is present as a pharmaceutically acceptable salt or solvate thereof.

In another embodiment, the (S) enantiomer is additionally or alternatively present in the composition. This (S)-3-(5-fluoro-1H-indol-3-yl)pyrrolidine-2,5-dione enantiomer is characterized by the structure of Formula II":

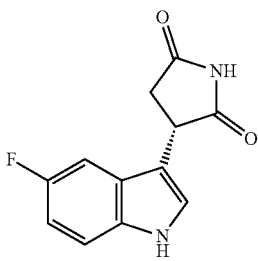

II'' which is in free base form. Optionally, the compound is present as a pharmaceutically acceptable salt or solvate thereof. Pharmaceutical compositions may contain mixtures of the compounds of Formula II' and Formula II''.

These compounds have been found to have the biological activity provided in Table 1 below.

and for PF-06840001 (inactive) were 0.21 and 0.56, respectively. These results indicate that CNS compartments are accessible. Human PK Prediction: After oral administration of the racemate, the active enantiomer has a predicted $CL_p$ of 0.64 ml/min/kg and a $V_{ss}$ of 1.03 L/kg with a $t_{1/2} \approx 19$ hours. The bioavailability of the active enantiomer after an oral dose of the racemate is projected to be 64%.

From the studies conducted to date, it may be concluded that the racemate is a selective IDO1 inhibitor with very favorable PK characteristics. The compound reduced Kynurenine (Kyn) level in plasma and tumors. The compound has a prolonged projected human half-life of $t_{1/2}$ of about 19 hrs, which should allow once a day administration. The compound has CNS penetration for potential impact on brain metastases. Further, checkpoint antagonists/agonists against PD-L1, CTLA4 and 4-1BB cause enhanced IDO1 expression and activity. The compound exhibited enhanced in vivo anti-tumor efficacy in combination with anti-PD-L1,

| Assay | PF-06840003 (Compound 1) | PF-06840002 (Compound 2) (μM) | PF-06840001 (Compound 2a) |
|---|---|---|---|
| Enzyme Activity:[a] $IC_{50}$ | | | |
| human IDO1 | 0.41 (0.30-0.54) | 0.20 (0.16-0.26) | >10 |
| mouse IDO1 | 1.5 (1.3-1.7) | 0.73 (0.70-0.76) | NT |
| dog IDO1 | 0.59 (0.37-0.95) | 0.20 (0.12-0.33) | NT |
| human TDO2 | >50 | >50 | >50 |
| mouse TDO2 | >50 | >50 | >50 |
| Binding[a] | | | |
| Ferrous form human IDO1; $K_d^{app}$ | 14 (12-16) | 6 (3-12) | |
| Ferric form (—$O_2$) human IDO1; $K_d^{app}$ | 0.32 (0.27-0.38) | 0.16 (0.13-0.19) | |
| Cellular Activity | | | |
| HeLa cells (+ IFNγ) IDO1 $IC_{50}$ ± SD (n) | 1.8 ± 0.7 (13) | 1.0 ± 0.4 (11) | 12.8 ± 6.3 (5) |
| THP-1 cells (+ IFNγ/LPS) IDO1 $IC_{50}$ ± SD (n) | 1.7 ± 0.6 (9) | 1.1 ± 0.4 (11) | 5.8 ± 2.6 (5) |
| T-cell proliferation in SKOV3 co-culture system (50% serum) IDO1 $IC_{50}$ ± SD (n) | 0.07 | 0.08 ± 0.05 (3) | |
| A172 and THP-1 cells TDO2 | no inhibition @50 | no inhibition @50 | |
| Human whole blood (+ IFNγ/LPS) IDO1 $IC_{50}$ ± SD (n = 10); unbound | | 1.1 ± 0.7 | |

The racemic 3-(5-fluoro-1H-indol-3-yl)pyrrolidine-2,5-dione compound was evaluated for off target pharmacological activity in a panel of receptors, ion channels, transporters and enzymes (64 targets in total) in the Cerep Wide Ligand Profile Screen at an initial concentration of 200 μM. Three hits were noted (defined by a response greater that 50% of a maximal response) and follow up curves were performed by Cerep. The results suggest a low potential for secondary (off-target) pharmacology.

This racemic compound has also been found to have the following pharmacokinetic characteristics. In vitro Absorption: passive permeability was evaluated in Ralph-Russ canine kidney (RRCK) cells; high intrinsic permeability with an apical to basolateral (A to B) value of 25.5×10$^{-6}$ cm/sec. CNS Penetration: CNS distribution was investigated in male rats. Unbound AUC ratios of brain to plasma and CSF to plasma of PF-06840002 (active) were 0.20 and 0.49, CTLA4 and 4-1BB. More particularly, IDO/kyn level is normalized in tumor after co-administration with aPD-L1, anti-CTLA4, or anti-4-1BB. Further, a higher proportion of IFNγ secreting tumor cells was observed in tumor treated with the racemate and anti-PD-L1 combined.

A variety of ratios of the two compounds may be selected. For example, the ratio may be about 1:1, or the compound of Formula II' may be present in greater than 50%, greater than 95%, greater than 90%, or about 95% to 100%. Similarly, in other compositions, the compound of Formula II'' may be present in greater than 50%. The discussion of suitable ratios and molar percentages of enantiomers relating to the compounds of Formula I and its subformulae earlier in the specification, is hereby incorporated by reference.

As described herein, reference to Formula II, II' and II'', include reference to their deuterated counterparts, unless otherwise specified. As described herein, a racemic compound of Formula II may contain about 50% of a compound of Formula II' and about 50% of Formula II" based on a molar ratio (about 48 to about 52 mol %, or about a 1:1 ratio)) of one of the isomers. In another embodiment, a composition, medicament, or method of treatment may involve combining separately produced compounds of Formula II' and Formula II" in an approximately equal molar ratio (about 48 to 52%). In another embodiment, a medicament or pharmaceutical composition may contain a mixture of separate compounds of Formula II' and Formula II" in different ratios. In one embodiment, the pharmaceutical composition contains an excess (greater than 50%) of the R-enantiomer (Formula II'). Suitable molar ratios of R/S may be from about 1.5:1, 2:1, 3:1, 4:1, 5:1, 10:1, or higher. In another embodiment, a pharmaceutical composition may contain an excess of the S-enantiomer (Formula II"), with the ratios provided for R/S reversed. Other suitable amounts of R/S may be selected. For example, the R-enantiomer may be present in amounts of at least about 55% to 100%, or at least 65%, at least 75%, at least 80%, at least 85%, at least 90%, about 95%, about 98%, or 100%. In other embodiments, the S-enantiomer may be present in a higher percentage, e.g., in amounts of at least about 55% to 100%, or at least 65%, at least 75%, at least 80%, at least 85%, at least 90%, about 95%, about 98%, or 100%. Ratios between all these exemplary embodiments as well as greater than and less than them while still within the invention, all are included. (The term "ratio" as used herein (above and below) refers always to the molar ratio). Compositions may contain a mixture of the racemate and a separate compound of Formula II' and/or Formula II", in free base and/or in salt form.

Optionally, the racemate, or one or both of the enantiomers, may be deuterated. As with the racemate, a deuterated enantiomer may be in free base, or optionally, in salt or solvate form. An illustrated deuterated racemic compound (3-$^2$H)-3-(5-fluoro-1H-indol-3-yl)pyrrolidine-2,5-dione is provided in the examples below. Other deuterated compounds may include, e.g., (−)-(R)-(3-$^2$H)-3-(5-fluoro-1H-indol-3-yl)pyrrolidine-2,5-dione:

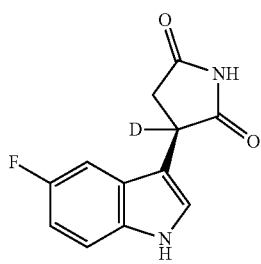

IIa' and (+)-(S)-(3-$^2$H)-3-(5-fluoro-1H-indol-3-yl)pyrrolidine-2,5-dione:

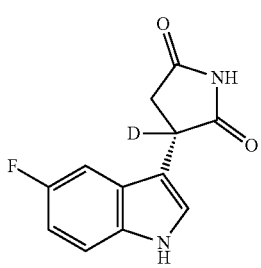

IIa"

Without wishing to be bound by theory, one enantiomer (isomer or stereoisomer) can convert in plasma to the racemate and/or to the other enantiomer. It is believed that deuteration at the chiral center of these compounds slows the conversion of the individual stereoisomers to the racemate and/or the other stereoisomer in plasma.

These compounds were named using ChemBioDraw® Ultra version 12.0 (PerkinElmer).

The IDO1 inhibitory compounds thereof contain an asymmetric center and thus exist as different stereoisomeric forms. Accordingly, the combinations may include all possible stereoisomers and includes not only racemic compounds but the individual enantiomers and their non-racemic mixtures as well. When a composition is desired to contain a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The IDO1 inhibitory compounds may be in the form of pharmaceutically acceptable salts. The term "pharmaceutically acceptable salt" is intended to include all acceptable salts such as can be used as a dosage form for modifying the solubility or hydrolysis characteristics or can be used in sustained release or pro-drug formulations. Pharmaceutically acceptable salts of the compounds of Formula II include base salts, which form non-toxic salts including, e.g., aluminum, calcium, choline, magnesium, potassium, sodium, zinc, and tetramethylammonium hydroxide. Although less desired, other bases may be selected, including, e.g., ammonia, ethylenediamine, N-methyl-glutamine, lysine, arginine, ornithine, N,N'-dibenzylethylene-diamine, chloroprocaine, diethanolamine, procaine, N-benzylphenethyl-amine, diethylamine, piperazine, tris(hydroxymethyl) aminomethane, benzathine, diethylamine, diolamine, glycine, lysine, meglumine, olamine, tromethamine, 2-(diethylamino)ethanol, ethanolamine, morpholine, and 4-(2-hydroxyethyl)morpholine. Hemisalts of bases may also be formed, for example, hemicalcium salts.

Pharmaceutically acceptable salts of the IDO1 compounds described herein may be prepared by one or more of these methods:
 (i) by reacting the compound of Formula II with the desired base;
 (ii) by removing an acid- or base-labile protecting group from a suitable precursor of the compound of Formula II or by ring-opening a suitable cyclic precursor, for example, a lactone or lactam, using the desired acid; or
 (iii) by converting one salt of the compound of Formula II to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized. These salts may be prepared by standard procedures, e.g. by reacting a free acid with a suitable organic or inorganic base. Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

In addition, although generally, free bases are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula II above.

As used herein, the term "free base" refers to the non-salt form of a compound of the 3-(5-fluoro-1H-indol-3-yl)pyrrolidine-2,5-dione compound (the compound of Formula II).

Pharmaceutically acceptable predrugs and prodrugs of the 3-(5-fluoro-1H-indol-3-yl)pyrrolidine-2,5-dione compound (the compound of Formula II) may also be utilized.

As used herein, a PD-L1 antagonist or inhibitor is any moiety and blocks interaction of Programmed Cell Death Protein 1 Ligand (PD-L1) which is expressed on certain tumor cells and other immune cells with its receptor PD-1 located on activated T cells, B cells and myeloid cells. Such an antagonist may be a small molecule drug (e.g., CA-170; Curis Inc) or an anti-PD-L1 antibody. As used herein, an anti-PD-L1 antibody is any immunoglobulin which binds the PD-L1 ligand and blocks interaction of Programmed Cell Death Protein 1 Ligand (PD-L1) which is expressed on certain tumor cells and other immune cells with its receptor PD-1 located on activated T cells, B cells and myeloid cells. Examples of such anti-PD-L1 antibodies may include, e.g., avelumab (formerly MSB0010718C, Merck/Pfizer) or the antibodies described in WO 2013/079174A1 and US 2014/0241917, which is incorporated by reference (Merck), or MED14736 (AstraZeneca) [described in WO2011/066389 and US2013/034559], or lambrolizumab.

An anti-PD-1 antibody in any immunoglobulin which binds to PD-1 and blocks the interaction with its ligands, PD1 and PD2. In certain embodiments, another class of anti-PD-1 antagonists (e.g., a small molecule) may be substituted for the anti-PD-1 antibody.

The term "antibody" includes monoclonal antibodies (including full length antibodies which have an immunoglobulin Fc region), antibody compositions with polyepitopic specificity, multispecific antibodies {e.g., bispecific antibodies, diabodies, and single chain molecules, as well as antibody fragments (e.g., Fab, F(ab')2, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain 30 disulfide bridges. Each H chain has at the N-terminus, a variable domain (VH) followed by three constant domains (CH) for each of the α and γ chains and four CH domains for μ and E isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds}, Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA 1 and IgK1.

In one embodiment, the anti-PD-L1 antibody is avelumab [CAS Registry Number 1537032-82-2; FDA UNII KXG2PJ551I]. Avelumab is a fully human anti-PD-L1 IgG1 monoclonal antibody which is available from Merck/Pfizer. See, e.g., WO 2013/079174 for the sequences of clone A-09-262-2 and methods of manufacturing and purification thereof, which are incorporated by reference herein. See, also, heavy chain SEQ ID NO: 1: EVQLLESGGG LVQPGGSLRL SCAASGFTFS SYIMMWVRQA PGK-GLEWVSS IYPSGGITFY ADTVKGRFTI SRDNSKNTLY LQMNSLRAED TAVYYCARIK LGTVTTVDYW GQGTLVTVSS ASTKGPSVFP LAPSSKSTSG GTAAL-GCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPE-VKFNW YVDGVEVHNA KTKPREEQYN STYRVVSVLT VLHQDWLNGK EYKCKVSNKA LPA-PIEKTIS KAGGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK Light chain: SEQ ID NO: 2:
QSALTQPASV SGSPGQSITI SCTGTSSDVG GYNYVSWYQQ HPGKAPKLMI YDVSNRPSGV SNRFSGSKSG NTASLTISGL QAEDEADYYC SSYTSSSTRV FGTGTKVTVL GQPKANPTVT LFPPS-SEELQ ANKATLVCLI SDFYPGAVTV AWKADGSPVK AGVETTKPSK QSNNKYAASS YLSLTPEQWK SHRSY-SCQVT HEGSTVEKTV APTECS. In certain embodiments, the anti-PD-L1 antibody is characterized by having a heavy chain with the amino acid sequence of SEQ ID NO: 24 (first 120 amino acids in SEQ ID NO: 1, above) and the light chain having the amino acid of SEQ ID NO: 25 (first 110 amino acids in SEQ ID NO: 2, above) of WO 2013/079174.

Uses

A combination therapy is provided herein comprising at least one 3-(5-fluoro-1H-indol-3-yl)pyrrolidine-2,5-dione compound (i.e. a racemic compound of Formula II) as a first active ingredient and at least one second, different, active component which is an anti-PD-L1 antibody as defined above. Optionally, a third, or additional active ingredients may be selected which are from a different class of compounds than the IDO inhibitor and the anti-PD-L1 inhibitor. In certain embodiments, more than one IDO inhibitor may be used in the combination. Alternatively, the combination therapy utilizes the R-enantiomer (Formula II'). In still another alternative, a mixture of (R)- and (S)-enantiomers may be selected for use. Optionally, these racemic, or enantiomeric, compounds may be deuterated, e.g., at the chiral center. In still another alternative, a mixture of a racemic compound and one or both of the enantiomers is used in a combination with the anti-PD-L1 antibody and the optional at least third active component.

Typically, in such combination therapies, the at least one 3-(5-fluoro-1H-indol-3-yl)pyrrolidine-2,5-dione compound and the anti-PD-L1 antibody, and optional third, different active component are formulated into separate pharmaceutical compositions or medicaments. When separately formulated, the at least two active components can be administered simultaneously or sequentially as separate dosage forms, optionally via different routes.

In one embodiment, the at least one at least one 3-(5-fluoro-1H-indol-3-yl)pyrrolidine-2,5-dione compound is delivered to a subject in an amount ranging from about 0.025 mg/kg to 600 mg/kg, or about 1 mg/kg to about 250 mg/mg, or a daily dose of about 10 mg to about 5000 mg, about 20 mg to about 1200 mg, or about 25 mg to about 800 mg, about 30 mg to about 675 mg, or about 400 mg to about 600 mg. However, higher or lower amounts may be selected depending upon the combination partner (i.e., the other active components). If the drug is formulated for or delivered by a non-oral route, it may be desirable to decrease the unit or daily dose amounts delivered. Thus, a combination regimen may involve as one of the active components, a racemic 3-(5-fluoro-1H-indol -3-yl)pyrrolidine-2,5-dione, (R)-3-(5-fluoro-1H-indol-3-yl)pyrrolidine-2,5-dione, (S)-3-(5-fluoro-1H-indol-3-yl)pyrrolidine-2,5-dione, (3-$^2$H)-3-(5-fluoro-1H-indol-3-yl)pyrrolidine -2,5-dione, (R)-(3-$^2$H)-(3-(5-fluoro-1H-indol-3-yl)pyrrolidine-2,5-dione, (S)-(3-$^2$H)-(3-(5-fluoro-1H-indol-3-yl)pyrrolidine-2,5-dione, or mixtures thereof.

For administration of an anti-PD1 or an anti-PD-L1 Ab in combination with the IDO1 inhibitor provided herein, the dosage can range from about 0.01 to about 20 mg/kg, about 0.1 to about 10 mg/kg, about 0.1 to about 5 mg/kg, about 1 to about 5 mg/kg, about 2 to about 5 mg kg, about 7.5 to about 12.5 mg/kg, or about 0.1 to about 30 mg/kg of the subject's body weight. For example, dosages can be about 0.1, about 0.3, about 1, about 2, about 3, about 5 or about 10 mg/kg body weight, or, about 0.3, about 1, about 2, about 3, or about 5 mg kg body weight, The dosing schedule is typically designed to achieve exposures that result in sustained receptor occupancy (RO) based on typical pharmacokinetic properties of an Ab. An exemplary treatment regime entails administration about once per week, about once every 2 weeks, about once every 3 weeks, about once every 4 weeks, about once a month, about once every 3-6 months or longer. In certain embodiments, an anti-PD-1 antibody or anti-PD-L1 antibody such as avelumab is administered to the subject about once every 2 weeks. In other embodiments, the Ab is administered about once every 3 weeks. The dosage and scheduling can change during a course of treatment. When used in combinations with the IDO inhibitor and other optional immunomodulatory/cancer agents, the dosage of the anti-PD-1 Ab or anti-PD-L1 Ab can be lowered compared to the monotherapy dose. For example, a dosage of avelumab that is lower than about 3 mg/kg about every 3 weeks, for instance about 0.1 mg/kg or less about every 3 or 4 weeks, is regarded as a subtherapeutic dosage. In certain embodiments, the dose of an anti-PD-1 antibody or anti-PD-L1 antibody is a fixed dose in a pharmaceutical composition. In other embodiments, the method of the present invention can be used with a flat dose (a dose given to a patient irrespective of the body weight of the patient).

However, it may be desirable in certain situations to formulate the at least one 3-(5-fluoro-1H-indol-3-yl)pyrrolidine-2,5-dione compound and the anti-PD-L1 antibody and/or one of these compounds and a third, different active component into a single formulation. Thus, according to one embodiment, pharmaceutical compositions and combinations which contain, in addition to a 3-(6-5-fluoro-1H-indol-3-yl)pyrrolidine-2,5-dione compound, additional therapeutic agents and/or active ingredients.

In certain embodiments, the combination of an anti-PD-1 Ab and IDO1 inhibitor, or anti-PD-L1 antibody and IDO inhibitor, are administered intravenously to the subject in an induction phase about every 2 or 3 weeks for 1, 2, 3 or 4 administrations. In certain embodiments, the combination is administered intravenously in the induction phase about every 3 weeks for about 4 administrations. The induction phase is followed by a maintenance phase during which only the anti-PD-1 or anti-PD-L1 antibody is administered to the subject at a dosage of about 0.1, about 0.3, about 1, about 2, about 3, about 5 or about 10 mg/kg every two or three weeks for as long as the treatment proves efficacious or until unmanageable toxicity or disease progression occurs.

The combinations provided herein utilize pharmaceutical compositions or medicaments comprising a compound and/or drug and at least one pharmaceutically acceptable carrier, diluent, excipient and/or adjuvant. The carrier(s) are "acceptable" in the sense of being compatible with the other ingredients of the formulation and, in the case of a pharmaceutically acceptable carrier, not deleterious to the recipient thereof in an amount used in the medicament.

In addition to the combination of the at least one 3-(5-fluoro-1H-indol-3-yl)pyrrolidine -2,5-dione compound and the anti-PD-1 or anti-PD-L1 antibody, optionally such a combination may contain one or more additional pharmaceutical agents or treatment methods such as, for example, an immunomodulatory agent. An immunomodulatory agent may include, e.g., an immunosuppressant or an immune enhancer. Such immunomodulatory agents may include, e.g., an anti-PD-1 antibody (e.g., pembrolizumab, nivolumab), a CTLA-4 antibody, antibodies directed against tumor-necrosis factor (TNF) receptors 4-1BB and Ox40 (e.g., an anti-OX-40 antibody or anti -4-1BB antibody), an anti-cancer antigen vaccine, a P-cadherin LP-Dual-Affinity Re-Targeting protein, a TDO inhibitor [see, e.g., Ser. No. 14/076,016, filed Nov. 8, 2013, now published as US 2015/0133422A1; U.S. patent application Ser. No. 14/619,589, filed Feb. 11, 2015, now published as US 2015/0225367A1; and U.S. patent application Ser. No. 14/660,082, filed Mar. 17, 2015, now published as US 2015/0266857], or an antibody-drug conjugate (ADC). While some of the working examples below utilize a murine antibody, such an antibody is better adapted for study in a murine model system which is representative of the effect which will be observed in human patients. Thus, for use in the anti-cancer (antineoplastic) combinations provided herein, a humanized or fully human monoclonal antibody may be preferred. In one embodiment, the immunomodulatory agent is an anti-CTLA4 antibody, e.g., tremelimumab (formerly CP -675, 206, a full human IgG2 Mab); ipilimumab (MDX-0120; Medarex; Bristol-Myers Squibb. Other immunomodulatory compounds may include axitinib, crizotinib, second-generation anaplastic lymphoma kinas (ALK) inhibitors. In another aspect, the second active agent is p53 cancer vaccine, p53 epitope vaccine, and other cancer vaccines (e.g., to activate dendritic cells).

Other immunomodulatory compounds may include cytokine therapy (e.g., an interleukin (IL) such as IL-2, gamma interferon, beta interferon, or GM-CSF), and/or tyrosine kinase inhibitors. For example, ibrutinib [also known as PCI-32765, currently marketed by Janssen Pharmaceuticals for oral administration under the name Imbruvica®] is a TEC kinase family inhibitor, including Bruton's tyrosine kinase (BTK).

Yet other immunomodulatory compounds may include anti-cancer agents which block immune cell migration such as antagonists to chemokine receptors, including CCR2 and CCR4, or anti-viral agents, chemotherapeutics or other anti-cancer agents, radiation, anti-tumor and anti-viral vaccines.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, gemcitabine, 5-fluorouracil (5-FU), doclitaxel, and temozolomide.

The combinations described herein may further be used in combination with vaccine therapy. Anti-cancer vaccines include dendritic cells, synthetic peptides, DNA vaccines and recombinant viruses. One example is an anti-p53 vaccine, e.g., which may be delivered via a replication-defective adenovirus vector.

A combination as provided herein may include co-administration of a 3-(5-fluoro-1H-indol-3-yl)pyrrolidine-2,5-dione compound, an anti-PD-1 or anti-PD-L1 antibody, and at least one signal transduction inhibitor (STI). A "signal transduction inhibitor" is an agent that selectively inhibits one or more vital steps in signaling pathways, in the normal function of cancer cells, thereby leading to apoptosis. Signal transduction inhibitors (STIs) include, but are not limited to, bcr/abl kinase inhibitors such as, for example, Imatinib mesylate (formerly STI 571, Gleevec or Glivec); epidermal growth factor (EGF) receptor inhibitors such as, for example, kinase inhibitors (Iressa, SSI-774) and antibodies (Imclone: C225 and Abgenix: ABX-EGF); her-2/neu receptor inhibitors such as, for example, Herceptin™ (trastuzumab), and farnesyl transferase inhibitors (FTI) such as, for example, lonafarnib (CAS No. 193275-84-2); manumycin A, tpifarnib, and GGTI-297); inhibitors of Akt family kinases or the Akt pathway; inhibitors of the phosphatidyl inositol kinase inhibitors (Pi3K), a Pi3K-alpha selective inhibitor, and mTOR pathway, such as, for example, the mTOR inhibitor rapamycin (sirolimus) or temsirolimus; a MEK inhibitor, an inhibitor of an enhancer of zeste homolog 2 (EZH2), cell cycle kinase inhibitors such as, for example, flavopiridol; an epidermal growth factor (EGFR) inhibitor, a vascular endothelial growth factor (VEGF) inhibitor, or a selective inhibitor of the cyclin-dependent kinases CDK5 and CDK6. In a particular embodiment, the STI is selected from the group consisting of STI 571, SSI-774, C225, ABX-EGF, trastuzumab, L-744, 832, rapamycin, LY294002, flavopiridal, and UNC-01.

Also provided is a method for treating a chronic viral infection in a patient by administering a combination as provided herein. Particularly desirable viral infection include those associated with oncogenic properties. Examples of such viral infections may include, e.g., human papilloma virus (HPV) (cervical cancer), human immunodeficiency virus (HIV) (e.g., Kaposi carcoma, cervical cancer, non-Hodgkin lymphoma, anal cancer, Hodgkin disease, lung cancer, cancers of the mouth and throat, skin cancer, liver cancer), herpes simplex virus (HSV) (liver cancer), non-Hodgkin lymphoma); human herpes virus 8 (Kaposi sarcoma-associated); human T-lymphotrophic virus-1 (HTLV-1) (e.g., lymphocytic leukemia and adult T-cell leukemia/lymphoma (ATL)); merkel cell polyomavirus (skin cancers); and Epstein-Barr virus (EBV) (nasopharyngeal cancer, lymphoma including Burkitt lymphoma, Hodgkin lymphoma, stomach center), varicella zoster virus, and coxsackie virus), simian virus 40 (e.g., mesothelioma, brain tumors, bone cancers and lymphomas), among other.

By means of non-limiting examples, the compounds, anti-PD-1 or anti-PD-L1 antibody, and any other optional active drugs may be formulated as separate pharmaceutical preparations, as a single pharmaceutical preparation, or mixtures thereof. Any suitable form may be selected, e.g., in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, disintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations are preferably in a unit dosage form, and may be suitably packaged, for example in a box, blister, vial, bottle, sachet, ampoule or in any other suitable single-dose or multi-dose holder or container (which may be properly labeled); optionally in a kit which also comprises with one or more leaflets containing product information and/or instructions for use.

Depending on the condition to be prevented or treated and the route of administration, each of the different active compounds may be independently administered as a single daily dose, divided over one or more daily doses, or essentially continuously, e.g. using a drip infusion.

Also provided herein is use of combinations in the treatment and/or prevention of cancer or endometriosis. In one embodiment, combinations provide herein are useful in increasing immune recognition and destruction of the cancer cells. In one embodiment, in a combination provided herein, the IDO1 inhibitory compound and/or the anti-PD-1 or anti-PD-L1 components enhances the activity of at least a third active component.

The combinations herein are useful as medicaments, in particular in the prevention and/or treatment of cancer.

Various cancers are known in the art. The cancer may be metastatic or non-metastatic. The cancer may be may be familial or sporadic. In some embodiments, the cancer is selected from the group consisting of: leukemia and multiple myeloma. In one embodiment, the cancer is leukemia. In one embodiment, the cancer is multiple myeloma.

Additional cancers that can be treated using the methods provided herein include, for example, benign and malignant solid tumors and benign and malignant non-solid tumors. In one embodiment, the cancer is benign solid tumors. In one embodiment, the cancer is malignant solid tumors. In one embodiment, the cancer is benign non-solid tumors. In one embodiment, the cancer is malignant non-solid tumors.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

In one embodiment, the cancer is biliary tract cancer. In one embodiment, the cancer is brain cancer, including gliomas, glioblastomas and medulloblastomas. In one embodiment, the cancer is breast cancer. In one embodiment, the cancer is cervical cancer. In one embodiment, the cancer is choriocarcinoma. In one embodiment, the cancer is colon cancer. In one embodiment, the cancer is endometrial cancer. In one embodiment, the cancer is esophageal cancer. In one embodiment, the cancer is gastric cancer. In one embodiment, the cancer is intraepithelial neoplasms, including Bowen's disease and Paget's disease. In one embodiment, the cancer is liver cancer. In one embodiment, the cancer is lung cancer. In one embodiment, the cancer is neuroblastomas. In one embodiment, the cancer is oral cancer, including squamous cell carcinoma. In one embodiment, the cancer is ovarian cancer, including those arising from epithelial cells, stromal cells, germ cells and mesenchymal cells. In one embodiment, the cancer is pancreatic cancer. In one embodiment, the cancer is prostate cancer. In one embodiment, the cancer is rectal cancer. In one embodiment, the cancer is renal cancer, including adenocarcinoma and Wilms tumour. In one embodiment, the cancer is sarcomas, including leiomyosarcoma, rhabdomyosarcoma, liposarcoma, fibrosarcoma and osteosarcoma. In one embodiment, the cancer is skin cancer, including melanoma, Kaposi's sarcoma, basocellular cancer and squamous cell cancer. In one embodiment, the cancer is testicular cancer including germinal tumors (seminomas, and non-seminomas such as teratomas and choriocarcinomas. In one embodiment, the cancer is stromal tumors. In one embodiment, the cancer is germ cell tumors. In one embodiment, the cancer is thyroid cancer, including thyroid adenocarcinoma and medullary carcinoma. In certain embodiments, the combinations provided herein are useful in treating brain metastases.

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In one embodiment, the lymphoid disorder is acute lymphocytic leukemia. In one embodiment, the lymphoid disorder is chronic lymphoproliferative disorders (e.g., lymphomas, myelomas, and chronic lymphoid leukemias). In one embodiment, the lymphoma is Hodgkin's disease. In one embodiment, the lymphoma is non-Hodgkin's lymphoma. In one embodiment, the lymphoma is lymphocytic lymphoma. In one embodiment, the chronic lymphoid leukemia is T cell chronic lymphoid leukemia. In one embodiment, the chronic lymphoid leukemia is B cell chronic lymphoid leukemia.

Also provided are a method for delaying in a subject the onset of cancer comprising the administration of a pharmaceutically effective amount of a combination as provided herein to a subject in need thereof.

Also provided is the use of combinations for modulating the IDO inhibitory activity of the 3-(5-fluoro-1H-indol-3-yl)pyrrolidine-2,5-dione) compound(s). Thus, according to a further feature is a method for enhancing IDO1 activity of the 3-(5-fluoro-1H-indol-3-yl)pyrrolidine-2,5-dione) compound(s), in a subject in need of such treatment, which comprises administering to said subject an effective amount of a combination provided herein.

The following terms have the following meanings:

The term "solvate" is used herein to describe a compound that contains stoichiometric or sub-stoichiometric amounts of one or more pharmaceutically acceptable solvent molecule such as ethanol. The term "hydrate" refers to when the said solvent is water.

The term "prodrug" as used herein means the pharmacologically acceptable derivatives of compounds of Formula II, such as for example amides, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease.

The term "human" refers to a person of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" (or more simply an "effective amount") as used herein means the amount of active agent or active ingredient that is sufficient to achieve the desired therapeutic or prophylactic effect in the subject to which/whom it is administered.

The term "administration", or a variant thereof (e.g. "administering"), means providing the active agent or active ingredient, alone or as part of a pharmaceutically acceptable composition, to the subject in whom/which the condition, symptom, or disease is to be treated or prevented.

By "pharmaceutically acceptable" is meant that the ingredients of a pharmaceutical composition are compatible with each other and not deleterious to the subject to which it is administered.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "IDO1 inhibitor" refers to a compound that has a biological effect to inhibit or significantly reduce or down-regulate the expression of the gene encoding for IDO1 and/or the expression of IDO1 and/or the biological activity of IDO1.

"D" and "d" both refer to deuterium. "dx.y" refers to substitution with from x to y number of deuterium atoms. "Stereoisomer" refers to both enantiomers and diastereomers. A group is "substituted with" a substituent when one or more hydrogen atoms of the group are replaced with a corresponding number of substituent atoms (if the substituent is an atom) or groups (if the substituent is a group). For example, "substituted with deuterium" refers to the replacement of one or more hydrogen atoms with a corresponding number of deuterium atoms.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

EXAMPLES

The present invention will be better understood with reference to the following examples. These examples are intended to representative of specific embodiments of the invention, and are not intended as limiting the scope of the invention.

I. CHEMISTRY EXAMPLES

The MS data provided in the examples described below were obtained as followed: Mass spectrum: LC/MS Agilent 6110 (ESI) or a Waters Acquity SQD (ESI)

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative HPLC purifications were performed with a mass directed autopurification Fractionlynx from Waters equipped with a Xbridge™ Prep C18 OBD column 19×150 mm 5 µm, unless otherwise reported. All HPLC purifications were performed with a gradient of $CH_3CN/H_2O/NH_4HCO_3$ (5 mM), $CH_3CN/H_2O/TFA$ (0.1%), or $CH_3CN/H_2O/NH_3$ $H_2O$ (0.1%).

Compound 1:
3-(5-fluoro-1H-indol-3-yl)pyrrolidine-2,5-dione

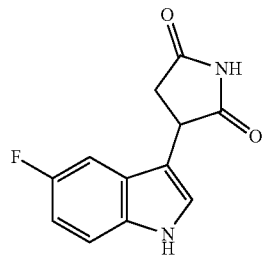 [SMILES: O=C1CC(c2c[nH]c3ccc(F)cc23)C(=O)N1]

A. Route A

A mixture of 5-fluoro-1H-indole (300 mg; 2.22 mmol), maleimide (646 mg; 6.65 mmol) in AcOH (2 mL) was stirred at 170° C. for 2 h in a microwave reaction. The reaction mixture was concentrated in vacuo. The residue was neutralized with saturated aqueous $NaHCO_3$ solution to pH 7~8 and extracted with EtOAc (10 mL×3). The combined organic layers were dried over anhydrous $Na_2SO_4$, filtered, concentrated, and purified by preparative HPLC to afford 180 mg (35%) of the title compound as a yellow solid. LC-MS for $C_{12}H_9FN_2O_2$—H⁻ [M–H]: calcd. 231.1; found: 231.0. $^1$H NMR (300 MHz, DMSO-$d_6$) δ [ppm]: 11.30 (brs, 1H), 11.14 (s, 1H), 7.41 (d, J=2.5 Hz, 1H), 7.36 (dd, J=9.0, 4.6 Hz, 1H), 7.20 (dd, J=10.1, 2.5 Hz, 1H), 6.94 (ddd, J=9.2, 9.0, 2.5 Hz, 1H), 4.33 (dd, J=9.5, 5.5 Hz, 1H), 3.17 (dd, J=18.0, 9.5 Hz, 1H), 2.79 (dd, J=18.0, 5.5 Hz, 1H).

Route B:

Alternatively, a mixture of 5-Fluoroindole (5.00 g, 5.00 g, 35.5 mmol, 96 mass %, 1.00) and Maleimide (1.5 equiv., 5.17 g, 53.3 mmol, 1.50) was charged in a 50 mL vessel, and then Acetonitrile (3 L/kg, 15.0 mL, 11.7 g, 286 mmol, 100 mass %) and Zinc Chloride (1.05 equiv., 5.08 g, 37.3 mmol, 100 mass %) were added. The reaction was heated to 85° C. over 10 min and then maintained at 85° C. for 24 hrs. While still at 85° C., Water (6 L/kg, 30.0 mL, 30.0 g, 1670 mmol, 100 mass %) was added slowly, while maintaining the temperature above 80° C. Yellow solids precipitated. The reaction mixture was cooled to 50° C. over 1 hour followed by stirring at 50° C. for 2 hours, then cooled 10° C. over 1 hour. The reaction was stirred at 10° C. for 1 hour. The solids were filtered off, then the filter cake was washed 2 times with 5 ml 1:1 ACN/water to afford isolated compound (6.85 g, 6.85 g, 29.5 mmol, 83.1% Yield).

For purification, the resulting isolated compound was charged (6.85 g, 6.85 g, 29.5 mmol, 100 mass %) into a vessel, followed by addition of Tetrahydrofuran (6 L/kg, 41.1 mL, 36.4 g, 505 mmol, 100 mass %). This mixture was heated to 66° C. to form a homogeneous solution. Heptane (4 L/kg, 27.4 mL, 18.7 g, 187 mmol, 100 mass %, was added slowly at 66° C.; solids began to precipitate after 5 volumes.

The mixture was cooled to 25° C. over 3 hours, then filtered and washed with heptane, followed by drying in the high vacuum oven overnight. Isolated compound (4.93 g, 4.93 g, 21.2 mmol, 100 mass %, 72.0% Yield).

This isolated compound is charged 2 (1.00 g, 4.3 mmol, 100 mass %,) into a 50 ml vessel And Tetrahydrofuran (6 L/kg, 6 mL, 100 mass %) and Heptane (6 L/kg, 6 mL, 100 mass %) were added. The slurry was stirred at 25° C. for 48 hrs. The solids were filtered off and dried in the high vacuum oven overnight. The Isolated compound: (0.89 g, 0.89 g, 3.83 mmol, 100 mass %, 89.00% Yield).

Compound 1a: (3-$^2$H)-3-(5-fluoro-1H-indol-3-yl) pyrrolidine-2,5-dione

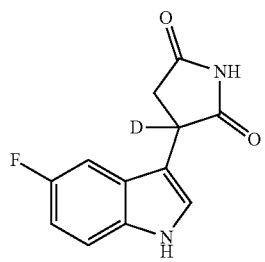 [SMILES: [2H]C1(c2c[nH]c3ccc(F)cc23)CC(=O)NC1=O]

To a solution of of 3-(5-Fluoro-1H-indol-3-yl)-pyrrolidine-2,5-dione (Compound 1, 200 mg, 0.87 mmol) in $D_2O$ (3 mL) was added $K_2CO_3$ (300 mg, 2.2 mmol). The reaction was stirred at 40° C. overnight. The mixture was extracted with EtOAc. The organic layer was dried, filtered, concentrated and purified by preparative HPLC to afford the Title Compound (20 mg, 10%) as a yellow solid. LC-MS for $C_{12}H_8DFN_2O_2$—H$^-$ [M−H]$^-$: calcd. 232.1; found: 232.1. $^1$H NMR (300 MHz, DMSO-d$_6$) δ [ppm]: 11.28 (s, 1H), 11.15 (s, 1H), 7.41 (d, J=2.1 Hz, 1H), 7.36 (dd, J=8.7, 4.5 Hz, 1H), 7.20 (dd, J=10.2, 2.4 Hz, 1H), 6.97-6.90 (m, 1H), 3.19-3.13 (m, 1H), 2.80-2.74 (m, 1H).

Compound 2: (−)-(R)-3-(5-fluoro-1H-indol-3-yl) pyrrolidine-2,5-dione

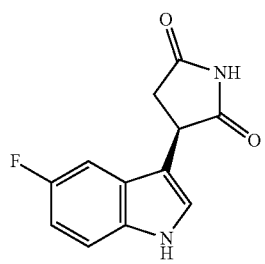 [SMILES: O=C1C[C@H](c2c[nH]c3ccc(F)cc23)C(=O)N1]

50 mg of the title compound was obtained as a yellow solid by chiral preparative HPLC separation of 150 mg of compound 1. Preparative chiral HPLC: Chiralpak® AS-H 250 mm×20 mm 5 µm; Mobile phase: $CO_2$/IPA=60/40; Flow: 50 mL/min 214 nm ambient temperature. Analytical chiral HPLC: Chiralpak® IC 250 mm×4.6 mm 5 µm; Mobile phase: Hexane/EtOH=70/30; Flow: 1.0 mL/min 230 nm ambient temperature; Retention time: 6.25 min. P1: 96.3% e.e. $[\alpha]^{254}_D$=−75.4 (c=0.0014, MeOH). LC-MS for $C_{12}H_9FN_2O_2$+H$^+$[M+H]$^+$: calcd. 233.1; found: 233.1. $^1$H NMR (300 MHz, DMSO-d$_6$) δ [ppm]: 11.30 (brs, 1H), 11.14 (s, 1H), 7.41 (d, J=2.5 Hz, 1H), 7.36 (dd, J=9.0, 4.6 Hz, 1H), 7.20 (dd, J=10.1, 2.5 Hz, 1H), 6.94 (ddd, J=9.2, 9.0, 2.5 Hz, 1H), 4.33 (dd, J=9.5, 5.5 Hz, 1H), 3.17 (dd, J=18.0, 9.5 Hz, 1H), 2.79 (dd, J=18.0, 5.5 Hz, 1H).

Compound 2a: (+)-(S)-3-(5-fluoro-1H-indol-3-yl) pyrrolidine-2,5-dione

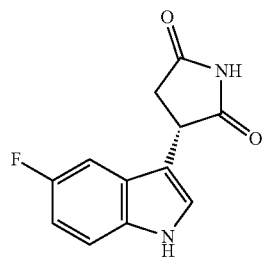

Isolated as second-eluting enantiomer from the chiral separation described for Compound 2a. Chiral HPLC retention time: 6.96 min. 98.5% e.e. $[\alpha]^{254}_D$=70 (c=0.0014, MeOH).

II. BIOLOGY EXAMPLES

II.1. Assay for IDO1 Enzymatic Activity Determination

The tested compounds inhibit the enzymatic activity of human IDO1.

To measure enzymatic activity of human IDO1, the reaction mixture contained (final concentrations) potassium phosphate buffer (50 mM, pH 6.5), ascorbic acid (10 mM), methylene blue (5 µM) and human recombinant IDO1 enzyme (prepared as described in Rohrig et al. J Med Chem, 2012, 55, 5270-5290; final concentration 5 µg/mL) without or with the IDO1 inhibitory compounds provided herein at the indicated concentrations (total volume 112.5 µL). The reaction was initiated by the addition of 37.5 µL of L-Trp (final concentration 100 µM) at room temperature. The reaction was conducted at room temperature during 15 minutes and stopped by the addition of 30 µL of 30% (w/v) trichloroacetic acid.

To convert N-formylkynurenine into kynurenine, the reaction mixture was incubated at 65° C. for 30 min. Then 120 µL of 2.5% (w/v) 4-(dimethylamino)-benzaldehyde in acetic acid were added and the mixture incubated for 5 min at room temperature. Kynurenine concentrations were determined by measuring the absorbance at 480 nm. A standard curve was made with pure kynurenine. The IDO1 activity was measured as described above using ten serial concentrations of the IDO1 inhibitory compounds provided herein. Data were fitted using the Prism software (GraphPad Software, Inc.).

Results from early testing of the biological activity of representative IDO1 inhibitory compounds is summarized in the following table:

| Compound | IC$_{50}$ (µM) |
| --- | --- |
| 1 | 0.15 |
| 1a | 0.21 |

-continued

| Compound | IC$_{50}$ (µM) |
|---|---|
| 2 | 0.12 |
| 2a | >50 |

More recent studies are reflected in the Table provided earlier in the specification. In one embodiment, compounds with an IC$_{50}$ below 5 µM are generally desirable to be selected for further study.

II.2.A Cellular Assay for IDO Activity Determination: hIDO1 P815 Cells

The compounds described herein inhibit the activity of human IDO in hIDO1 P815 cells [(ATCC® TIB-64™), *Mus musculus* mastocytoma cell)], available from American Type Culture Collection (ATCC), Manassas Va.].

The assay was performed in 96-well flat bottom plates seeded with P815 cells overexpressing hIDO1 (prepared as described in Rohrig et al. J Med Chem, 2012, 55, 5270-5290), at a concentration of 2×10$^5$ cells/well in a final volume of 200 µL. To determine IDO1 activity, the cells were incubated 24 hours at 37° C. at 5% CO$_2$ in IMDM (Invitrogen) supplemented with 2% FBS and 2% penicillin/streptomycin in the presence of the IDO1 inhibitory compounds provided herein, at different concentrations.

The plates were then centrifuged 5 min at 1000 rpm, and 100 µL of the supernatant were collected in a conical plate, 30 µL of TCA 30% were added and a further centrifugated at 3000×g for 10 minutes. 100 µL of the supernatant were collected in a flat bottomed plate and 100 µL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The IDO1 activity was measured as described above using ten different concentrations of the compounds provided herein. Data were fitted using the Prism software (GraphPad Software, Inc.).

The biological activity of representative compounds is summarized in the following table:

| Compound | IC$_{50}$ (µM) |
|---|---|
| 1 | 0.094 |
| 2 | 0.009 |
| 2a | 0.45 |

In one embodiment, compounds with an IC$_{50}$ below 5 µM are generally desirable to be selected for further study.

II.2.B Cellular Assay for IDO1 Activity Determination: HeLa Cells

The compounds provided herein inhibit the activity of human IDO1 in HeLa cells [human adenocarcinoma Cells,® CCL-2™].

The assay was performed in 96-well flat bottom plates seeded with the human cervical cancer HeLa cell line with stimulation with IFNγ.

To adhere HeLa cells (concentration of 5×10$^3$ cells/well) were incubated overnight at 37° C. at 5% CO$_2$ in EMEM (Lonza) supplemented with 10% FBS, 2% penicillin/streptomycin and 2 mM Ultraglutamin, in a final volume of 200 µL.

To stimulate the expression of IDO1, cells were then incubated two days at 37° C. at 5% CO$_2$ in EMEM (Lonza) supplemented with 2% FBS, 2% penicillin/streptomycin and 2 mM Ultraglutamine and 100 ng/mL IFNγ (R&D).

To determine IDO1 activity, medium was removed then the cells were incubated one day at 37° C. at 5% CO$_2$ in EMEM (Lonza) supplemented with 2% FBS and 2% penicillin/streptomycin in the presence of the IDO1 inhibitory compounds provided herein, at different concentrations. Then 100 µL of the supernatant were collected in a conical plate, 30 µL of TCA 30% were added and a centrifugation was made at 3000×g for 10 minutes. 100 µL of the supernatant were collected in a flat bottom plate and 100 µL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. Data were fitted using the Prism software (GraphPad Software, Inc.).

The biological activity of representative compounds is summarized in the following table:

| Compound | IC$_{50}$ (µM) |
|---|---|
| 1 | 1.0 |
| 2 | 0.77 |

In one embodiment, compounds with an IC$_{50}$ below 5 µM are generally desirable to be selected for further study.

II.2.C Assay for IDO1 Activity Determination in Human Blood: Whole Blood Leukocyte Concentrate The compounds provided herein inhibit the activity of human IDO1 in a human whole blood assay (whole blood leukocyte concentrate).

The human whole blood leukocyte concentrate was obtained as a byproduct in the manufacturing of red blood cell and platelet concentrate from a whole blood donation (as described in van der Meer et al., Vox Sang, 1999, 76(2), 90-99).

The assay was performed in 96-well flat bottom plates containing undiluted human whole blood leukocyte concentrate (with 2% penicillin/streptomycin) stimulated with lipopolysaccharide (LPS) (12.5 µg/mL) and recombinant human gamma interferon (rhIFNg) (50 ng/mL) for 18 hours to induce conversion of tryptophan to kynurenine. Plasma was collected after centrifugation and plasma kynurenine levels were determined LC-MS/MS (HPLC column Unison™ UK-Phenyl, 75×4.6, 3 µm, flow rate 0.8 mL/min, 4 minutes gradient from water+0.2% acetic acid to methanol+0.1% formic acid, retention time 2.7 min; API 4000™ MS-MS system from AB Sciex, ESI+mode, parent ion 209.2, daughter ion 94.1).

To determine the effect of IDO1 inhibition on kynurenine production, the compounds 1 and 2 were co-incubated at different concentrations. Data were fitted using the Prism software (GraphPad Software, Inc.).

The biological activity of representative compounds is summarized in the following table (results are the average of the results with blood from several different donors):

| Compound | IC$_{50}$ (μM) ± Standard Deviation | Number of individual blood donors |
|---|---|---|
| 1 | 3.36 ± 0.51 | 13 |
| 2 | 3.26 ± 0.71 | 15 |

II.2.D Cellular Assay for IDO1-Dependent T Cell Proliferation Determination: SKOV-3 PBMC Co-Culture The compounds provided herein restore T-cell proliferation in a SKOV-3 PBMC co-culture assay.

The assay was performed in 96-well flat bottom plates seeded with the human ovarian adenocarcinoma SKOV-3 cell line [SKOV-3; SKOV3] (ATCC® HTB-77™)] and co-cultured with human peripheral blood mononuclear cells (PBMC) stimulated with CD3/CD28 beads and rhIL-2.

To adhere, irradiated SKOV-3 cells (concentration of 150×10$^3$ cells/well) were incubated overnight at 37° C. at 5% CO$_2$ in Iscove's Modified Dulbecco's Medium (IMDM) (Lonza) supplemented with 50% FBS, 2% penicillin/streptomycin and 2 mM Ultraglutamin, in a final volume of 150 μL. Isolated PBMCs (stimulated with CD3/CD28 beads and rhIL-2 (30 U/mL)) were added in a ratio of 1:1. After 24 h of co-culture $^3$H-Thymidine (1 μCurie/10 μL) was added to assess proliferation (TopCount counter, Perkin Elmer) after overnight incubation in the presence of 50% serum.

To determine the effect of IDO1 inhibition on restoration of T cell proliferation, the compounds provided herein were co-incubated at different concentrations.

Compound 2 showed an EC$_{50}$ of 0.074 μM in this assay (average of three independent experiments).

II.3. In-Vivo Inhibition of Blood Kynurenine Levels in Healthy Mice

The compounds provided herein reduce the amount of Kynurenine in healthy mouse blood.

Briefly, mice were treated with either a suspension of one of the compounds provided herein in 0.5% hydroxypropyl methylcellulose (HPMC) K4M/0.25% Tween 20 at different doses, or with a vehicle control (0.5% HPMC K4M/0.25% Tween 20), by the oral route by gavage (dosing volume 5 mL/kg, 10 mice per group). After two hours, blood was harvested, plasma was prepared and the amount of Kynurenine present was determined by LC-MS-MS (HPLC column Unison UK-Phenyl, 75×4.6, 3 μm, flow rate 0.8 mL/min, 4 minutes gradient from water+0.2% acetic acid to methanol+ 0.1% formic acid, retention time 2.7 min; AP14000™ MS-MS system from AB Sciex, ESI+mode, parent ion 209.2, daughter ion 94.1).

Compound 1 inhibited circulating Kynurenine by 41% at 100 mg/kg (p<0.0001) and by 59% at 200 mg/kg (p<0.0001): see table below.

|  | Vehicle | Cpd. 1 100 mg/kg | Cpd. 1 200 mg/kg |
|---|---|---|---|
| Kynurenine concentration in plasma (average ± standard error of the mean) | 187.6 ± 17.8 ng/mL | 111.1 ± 27.0 ng/mL | 77.7 ± 9.2 ng/mL |

Compound 2 inhibited circulating Kynurenine by 39% at 10 mg/kg (p<0.0001), by 55% at 30 mg/kg (p<0.0001) and by 68% at 100 mg/kg (p<0.0001): see table below.

|  | Vehicle | Cpd. 2 10 mg/kg | Cpd. 2 30 mg/kg | Cpd. 2 100 mg/kg |
|---|---|---|---|---|
| Kynurenine concentration in plasma (average ± standard error of the mean) | 201 ± 15.7 ng/mL | 122 ± 3.5 ng/mL | 91.0 ± 4.4 ng/mL | 64.0 ± 3.8 ng/mL |

Example II.4: In Vivo Efficacy Studies in 4T1 Breast Cancer Syngeneic Model

In vivo efficacy studies were performed on 4T1 syngeneic tumor model of Balb/c mice implanted orthotopically in the mammary gland. One hundred thousand 4T1 breast cancer cells (ATCC® CRL-2539™)] were implanted orthotopically within the mammary gland of 7 weeks old Balb/c mice (day 0). Animals were randomized based on tumor size when tumor average reached 60 mm$^3$ (between day 7 and 11) into different treatment cohorts. The test compound was administered orally twice per day (approximately at 9 am and 5 μm) starting the day of randomization. The test compounds were suspended into Methocel™ cellulose ether vehicle and sonicated before oral administration to animals using gavage needles. Treatment was administered daily until the end of the study. All experimental animals were monitored for body weight changes twice weekly. Tumor volume was measured twice a week by a caliper device and calculated with the following formula: Tumor volume=0.5×(length×width$^2$). Studies were terminated before tumor volumes reached 2000 mm. TGI (% tumor growth inhibition) was determined as $$\left(1-\left(\frac{Tx-T0}{Cx-C0}\right)\right)*100.$$

The table below shows that Compound 1 inhibits 4T1 tumor growth in vivo.

| Treatment | Mean tumor volume (mm$^3$) on day 25 | TGI (Tumor growth inhibition) |
|---|---|---|
| Vehicle Methocel | 736.4 | 0% |
| Compound 1 100 mg/kg BID | 443.7 | 43.4% |

Example II.5: In Vivo Efficacy Studies with PancO2 Pancreatic Cancer Syngeneic Model In vivo efficacy studies were performed on PancO2 syngeneic tumor model of C57/Bl6 mice implanted sub-cutaneously. Five millions PancO2 pancreas cancer cells were implanted sub-cutaneously to 7 weeks old C57/Bl6 mice (day 0). Animals were randomized based on tumor size when tumor average reached 60 mm$^3$ (between day 10 and 12) into different treatment cohorts. The Compound was administered orally twice per day (approximately at 9 am and 5 pm) starting the day of randomization. The test compound shown below in the table was suspended into Methocel® vehicle and sonicated before oral administration to animals using gavage needles. Treatment was administered daily until the end of the study. All experimental animals were monitored for body weight changes weekly. Tumor volume was measured weekly using a caliper device and calculated with the following formula: Tumor volume=0.5×(length×width$^2$). Studies were terminated before tumor volumes reached 2000 mm. TGI (% tumor growth inhibition) was determined as $$\left(1-\left(\frac{Tx-T0}{Cx-C0}\right)\right)*100.$$

The table below shows that Compound 1 inhibits PancO2 tumor growth in vivo.

| Treatment | Mean tumor volume (mm$^3$) on day 42 | TGI (Tumor growth inhibition) |
|---|---|---|
| Vehicle Methocel | 598.2 | 0% |
| Compound 1 200 mg/kg BID | 457.0 | 26.2% |

In a separate study performed under the same conditions, Compound 2 (100 mg/kg BID) was studied. Methocel vehicle or 100 mg/kg of Compound 2 was administered orally twice per day (8 hours apart) starting the day of randomization. Compound 2 was resuspended into Methocel vehicle and sonicated before oral administration to animals using gavage needles. Treatment was administered daily until the end of the study. Tumor volume was measured weekly using a caliper device and calculated with the following formula: Tumor volume=0.5×(length×width$^2$). Mice were considered as dead when tumor size reached 400 mm$^3$. The table below show that Compound 2 inhibits PancO2 tumor growth in vivo. SEM refers to standard error of measurement.

| Treatment | Mean tumor volume (mm$^3$) +/− SEM on day 55 | TGI +/− SEM (Tumor growth inhibition) |
|---|---|---|
| Vehicle Methocel ® | 677.6 +/− 39.2 | 0% |
| Compound 2 - 100 mg/kg BID | 586.6 +/− 48.4 | 16.8% +/− 8.2 |

Example II.6: In Vivo Efficacy Studies on Inhibition of Tryptophan Degradation in 4T1 Tumor Tissue Compounds provided herein are capable of lowering kynurenine concentration within mouse tumors, for example 4T1 syngeneic tumors of Balb/c mice implanted orthotopically in the mammary gland. One hundred thousand 4T1 breast cancer cells were implanted orthotopically within the mammary gland of 7 weeks old Balb/c mice (day 0). Animals were randomized based on tumor size when tumor average reached 60 mm$^3$ (day 6) into different treatment cohorts (n=10/group). Animals were treated with Methocel vehicle from day 6 to 26 until tumors reached a size comprised between 1500 and 2000 mm$^3$. Compound 1 was suspended into Methocel vehicle and sonicated before oral administration to animals using gavage needles. Methocel vehicle or 200 mg/kg of Compound 1 was administered orally twice per day (approximately at 9 am and 5 μm) on day 26 and 27 days. The next morning, treatment was administered and mice were sacrificed 4 h after Compound 1 administration. The tumor was removed, weighted and frozen on dry ice. Tumors were analyzed by LC/MS-MS for Kynurenine concentration. Compound 1 reduced Kynurenine concentration by 47% (p<0.0001): see Table below.

| Treatment | Kynurenine concentration (ng/g tumor) Average ± SEM |
|---|---|
| Vehicle Methocel | 787.5 ± 46.2 |
| Compound 1 200 mg/kg | 417.2 ± 55.7 |

Example II.7: In Vivo Efficacy Studies on Inhibition of Tryptophan Degradation in CT26 Tumor Tissue A. Compounds Provided Herein are Capable of Lowering Kynurenine Concentration within Mouse Tumors In the present study, CT26 syngeneic tumors were implanted subcutaneously in Balb-c mice. More particularly, Five hundred thousand (500,000) CT26 colon carcinoma cancer cells [CT26.WT, available from the ATCC® CRL-2628™] were implanted subcutaneously in 7 weeks old Balb/c mice (day 0). Animals were randomized based on tumor size when tumor average reached 150 mm$^3$ (day 11) into different treatment cohorts (n=10/group). Compound 1 was suspended into Methocel™ (methylcellulose) vehicle and sonicated before oral administration to animals using gavage needles. Methocel vehicle or Compound 1 was administered orally twice per day (approximately at 9 am and 5 μm) at 200 mg/kg for 2 days to the mice, once the tumor reached a size comprised between 1500 and 2000 mm$^3$. The next morning, treatment was administered and mice were sacrificed 2 h after Compound 1 administration. The tumor was removed, weighted and frozen on dry ice. Tumors were analyzed by LC/MS-MS for Kynurenine concentration.

Compound 1 reduced Kynurenine concentration by 59% (p<0.0001): see Table below.

| Treatment | Kynurenine concentration (ng/g tumor) Average ± SEM |
|---|---|
| Vehicle Methocel | 2124 ± 272 |
| Compound 1 200 mg/kg | 876 ± 68 |

B. Compound 1 Inhibits Tumor Growth In Vivo.

In a separate study, anti-tumor efficacy of IDO-1 inhibition was tested in the colon syngeneic mouse tumor model CT26 with a range of different treatment regimens. The model was essentially as described above, except that 1×10$^6$ cells in phosphate buffered saline (PBS) were implanted subcutaneously in the flank of 8 week old Balb/c females on day 0 (10 in each group). Mice were randomized into treatment groups (100 mg/kg BID, 200 mg/kg BID or 600 mg/kg BID) based on tumor size on day 9 when treatment started. The results are shown the following table.

| Group | Dose mg/kg | Schedule | % TGI (D15) | % TGI (D17) | % TGI (D20) | N |
|---|---|---|---|---|---|---|
| Vehicle | — | BID | — | — | — | 10 |
| Compound 1 | 100 | BID | 29 | 33 | 20 | 10 |
| Compound 1 | 200 | BID | 38 | 41 | 34 | 10 |
| Compound 1 | 600 | BID | 36 | 51 | 38 | 10 |

At the highest dose of 600 mg/kg, BID a significant tumor growth inhibition (TGI) of up to 51%. At lower doses of 100 and 200 mg/kg BID, TGIs based on the group averages of tumor measurements are slightly lower and thus suggest a dose proportionality.

Example II.8: Activity of IDO Inhibitor PF06840003 (Compound 1)

A. Enzyme Assays

1. Expression and Purification of IDO1 Proteins

The full length complementary deoxyribonucleic acid (cDNA) for human IDO1 was cloned into a pFastbac-1 based vector and the full length cDNA for mouse and dog was cloned into a pET24a based vector. All constructs have a N-terminal cleavable His-tag and the nontagged IDO1 can be released by TEV protease treatment. Human IDO1 was expressed in insect cells and purified using Ni affinity column. The mouse and dog IDO1 were expressed in *Escherichia coli* BL21 (DE3) and purified using a Ni affinity column. To obtain non-tagged, pure, and hemin loaded IDO1, TEV protease treated and tag removed protein was incubated with 10× molar ratio of hemin (dissolved in 25 mM NaOH) to protein at 4° C. overnight followed by size exclusion chromatography (SEC) for human IDO1 and anion exchange and SEC for mouse and dog IDO1.

2. Measurement of Enzymatic Activity by Mass Spectrometry Assay

The inhibition of human, dog and mouse IDO1 was measured by quantitating tryptophan and the generation of kynurenine by MS. IDO1 enzyme (1 nM) was incubated with various concentrations of the inhibitor (50 mM to 1 nM), in duplicate, at room temperature in 100 mL buffer (Mg2+, Ca2+–PBS, 20 mM ascorbic acid, 10 mM methylene blue, 800 nM catalase, 15 mM tryptophan). After 22 minutes, 15 mL of 25% HCl was added to each well. The HCl stops the enzyme reactions and also converts the N-formyl kynurenine to kynurenine. Complete conversion occurred in less than 15 minutes at room temperature. Sealed plates were then transferred to a RapidFire 365 high throughput solid phase extraction (SPE) chromatography system coupled to a 6495 triple quadrupole mass spectrometer (Agilent Technologies, Santa Clara, Calif.). Detection of tryptophan and kynurenine was accomplished following injection of assay reaction (injection loop volume is 10 µL) onto an Agilent Graphite Type D cartridge in 0.01% trifluoroacetic acid (TFA) plus 0.09% formic acid and eluted using 80% acetonitrile, 0.09% formic acid and 0.01% TFA. The finalized RapidFire settings were as follows: aspiration time: 600 ms or until the loop is full per the sip sensor, load time: 5000 ms, elution time: 5000 ms, and re-equilibration time: 500 ms at a flow rate of 1.5 mL/min.

Following RapidFire SPE, samples were eluted into an Agilent 6495 triple quadrupole mass spectrometer with an Agilent Jet Stream source with ion funnel technology, set in positive ion mode. A multiple reaction monitoring (MRM) protocol was optimized employing Q1 m/z ratios of 205 and 209 for tryptophan and kynurenine, respectively. The second quadrupole (Q2) was used as a collision chamber employing house nitrogen as the collision gas. The third quadrupole (Q3) was set to select the product ions of tryptophan (m/z=188) and kynurenine (m/z=146). Fragmentor voltage was 380 V, collision energy (CE) was 10 V and cell accelerator voltage was 10 V. AUC for tryptophan and kynurenine was quantitated using RapidFire Integrator software (Agilent). Each compound was tested a minimum of three times against each species of purified IDO1 enzyme except for the dog enzyme where there were two replicates. Values displayed are the geometric means of all determinations (2 to 7 independent experiments)±95% confidence interval.

3. Measurement of Enzymatic Activity by Spectrophotometric Assay

Reaction solutions contained 120 mM L-tryptophan (Km 14 mM), 20 mM L-ascorbic acid, 10 mM methylene blue, 800 nM (500 U/mL) catalase, 1% DMSO (±inhibitor) in 200 mM phosphate buffer (pH 6.5). The assays were initiated with the addition of 30 nM human IDO1. The assay monitored the conversion of tryptophan to Nformyl-kynurenine as an increased absorbance at 326 nm ($\epsilon 321=3.75$ cm$^{-1}$ mM$^{-}$) at 21° C. on a Beckman DU800 spectrophotometer. IC50 was determined from an 11-point dose-response curve. Values displayed are the geometric means of two independent experiments ±95% confidence interval.

4. Inhibitor Mechanism Studies

Enzyme activity was measured using the enzymatic assay at various concentrations of both PF-06840003 and tryptophan in order to evaluate the mechanism of inhibition. Data were fit globally to models for competitive, non-competitive, uncompetitive and mixed inhibition. The model giving the best fit was either uncompetitive or non-competitive depending on the specific dataset and the enzyme species. To further inform mechanism, equilibrium binding studies were performed against different ferric and ferrous forms of human IDO1 and binding affinity was determined. Titrations of ferric and ferrous forms of human IDO1 with inhibitors were performed with either an open cuvette (ferric+$O_2$) or in an argon environment (ferric —$O_2$ and Ferrous) in a closed cuvette with a silicon septum. Typical binding conditions were 50 mM MOPS buffer (pH 7.0), 4.5 µM human IDO1 (with 100 fold excess dithionite ferrous form only), 100 µM Tryptophan (when used) at room temperature. Microliter volumes of titrant were added with a gas tight syringe. Analysis of the titration results for apparent inhibitor dissociation constant (Kdapp) values were carried out using double reciprocal plots on GraphPad Prism 6.0.

5. Human TDO2 Enzymatic Assay

The protocol was adapted from Dolusic et al, 2011. Briefly, the reaction mixture (150 mL) contained TRIS buffer (50 mM, pH 7.5), methylene blue (0.125 mM), ascorbic acid (0.25 M), catalase (40 units/mL) and human recombinant TDO2 enzyme (prepared as described in Dolusic et al, 2011; 0.9 mg) with increasing concentrations of compounds (1.0 nM to 50 mM). The reaction was run with single replicate. The reaction was initiated by the addition of the substrate L-tryptophan (1 mM). After 1 h of incubation, the reaction was stopped by addition of TCA (30% (w/v), and p-DMAB (2.5% (w/v) was added to convert N-formylkynurenine to kynurenine. Kynurenine concentrations were determined by measuring absorbance at 480 nm. Data were fitted and IC50 determined by using the PrismÔ software (GraphPad Software Inc.).

B. Cellular Assays

The HeLa human cervical carcinoma cell line and THP-1 human monocytic peripheral blood cell line were obtained from the American Type Culture Collection (ATCC). HeLa cells were maintained adherently in Eagles Minimal Essential Media (EMEM) with Earle's Balanced Salt Solution with no phenol red (Lonza) supplemented with 1 mM sodium pyruvate (Gibco-Life Technologies), 1× nonessential amino acids (Gibco-Life Technologies), 10% fetal bovine serum (FBS) (Sigma), 2 mM Ultraglutamine (Lonza), and penicillin-streptomycin (Gibco-Life Technologies). THP-1 cells were maintained in suspension in Roswell Park Memorial Institute (RPMI) medium (Gibco-Life Technologies) supplemented with 10 mM HEPES, 0.05 mM b-mercaptoethanol (Sigma), 10% FBS (Sigma), and penicillin-streptomycin (Gibco-Life Technologies). All cells were maintained in a humidified incubator at 37° C. with 5% carbon dioxide ($CO_2$).

The activity of PF-06840003 against hIDO1 was evaluated in THP-1 cells in parallel with its two enantiomers PF-06840002 (active) and PF-06840001 (inactive) in at least five independent experiments. hIDO1 activity was determined in the cells indirectly by cytokine induction and measurement of the relative amount of kynurenine levels secreted into media. THP-1 cells were treated with inhibitors from 50 µM to 0.847 in the presence of hIFNγ and LPS for 24 hours and allowed to catabolize tryptophan into kynurenine for detection. PF-06840003 racemate demonstrated activity against hIDO1 with a cellular $IC_{50}$ of 1658 nM, compared to the enantiomer PF-06840002 with an $IC_{50}$ of 1112 nM and PF-06840001 enantiomer with an $IC_{50}$ of 5844 nM. There was no appreciable decrease in THP-1 cell viability at concentrations up to 50 µM.

1. HeLa Cellular IDO1 Assay

To test the IDO1 activity in a cellular context, two human IDO1 inducible cell models were used. HeLa cells were harvested from cell culture flasks using 0.25% Trypsin/EDTA (Gibco-Life Technologies) and neutralized with EMEM growth medium. Following resuspension in fresh growth media, cells were seeded at 20,000 cells per well in 200 mL growth media in a 96-well plate and allowed to adhere at 37° C. at 5% $CO_2$ overnight. The following day, growth media was replaced with 200 mL reduced (2%) serum media containing 100 ng/mL recombinant human interferon gamma (rhIFNg) and incubated at 37° C. with 5% $CO_2$ for 48 hours to induce IDO expression. On day four, compounds were diluted to 10 mM in dimethylsulfoxide (DMSO), and 3-fold dilutions were prepared for an 11-point curve. rhIFNg-containing media was removed and following dilution into EMEM, compounds were added to cells at the highest concentration (50 mM to 0.847 nM) and allowed to incubate 16 to 24 hours at 37° C. with 5% $CO_2$ prior to final assay read-out.

Human IDO1 activity was also tested in the human peripheral blood-derived monocytic THP-1 cell line. THP-1 cells were resuspended into Iscove's Modified Dulbecco's media (IMDM) containing 4% FBS, plus 100 ng/mL lipopolysaccharide (LPS) and 50 ng/mL rhIFNγ to stimulate human IDO1 expression, then seeded at 100,000 cells per well in 100 µL in a 96-well plate. Compounds were diluted to 10 mM in DMSO. Eleven 3-fold dilutions beginning at 50 µM were prepared in IMDM medium and added to cells. Cells were incubated 16 to 24 hours at 37° C. with 5% $CO_2$.

For the assay read-out, that is identical for both cell lines, 100 mL of cell supernatant was transferred to a v-bottom 96 well plate. 30 mL 30% trichloroacetic acid (TCA) was added to each well to precipitate proteins, and plates were centrifuged at 3000 RPM for 10 minutes. 100 mL was transferred to a fresh flat-bottom 96-well plate and 100 mL/well of 2% 4-(dimethylamino)benzaldehyde (pDMAB) in acetic acid was added to derivatize N-formyl kynurenine to kynurenine for quantitative colorimetric readout. Assay plates were read at A492 on an Envision plate reader (Perkin Elmer). IC50 values were calculated using Activity Base software (Version 8.0.5.4) and non-linear regression of percent inhibition versus Log 10 concentration of IDO inhibitor compound. PF-06840003 was run in parallel and compared to PF-06840002 (active enantiomer), and PF-06840001 (inactive enantiomer).

2. TDO2 Activity Assay in A172 Cells

Compound 1 (PF-06840003) and isolated enantiomers (Compound 2 (PF-06840002 and PF-06840001) were evaluated in human TDO2 biochemical and cellular assays and in a murine TDO2 cellular assays. These inhibitors at concentrations of up to 50 µM did not display any significant inhibitory activity in any of the human or mouse TDO2 assays.

A172 cells were seeded in 96-well plates (12500 cells/well), treated with increasing concentrations of compounds and incubated for 16-18 h at 37° C., 5% $CO_2$. Then TCA was added to the supernatant to stop the reaction. p-DMAB was added to convert N-formylkynurenine to kynurenine. Kynurenine concentrations were determined by measuring absorbance at 480 nm. The reaction was run with single replicate.

3. TDO2 Activity Assay in THP-1 Cells

THP-1 cells were stimulated with 2 ng/ml PMA for 24 h, then seeded in 96-well plates (100,000 cells/well), treated with 2 ng/ml PMA and increasing concentrations of compounds, and incubated for 24 h. Kynurenine concentrations were determined as described above. The reaction was run with single replicate.

4. TDO2 Activity Assay in P815 mouseTDO2 Clone 12 Cells

P815 mTDO2 cl12 cells were generated as described in Pilotte et al, Proc Natl Acad Sci, 109(7): 2497-2502 (2012). They were seeded in 96-well plates (50,000 cells/well), treated with increasing concentrations of compounds and incubated for 16-18 h. Kynurenine concentrations were determined as described above. The reaction was run with single replicate.

5. Cell Viability Assay

Conditions in which kynurenine production is reduced will appear active in this assay. It is important to confirm cell viability at the assay endpoint. To test whether IDO inhibitor compounds affect cell viability during the IDO activity assays, cells were retained following removal of supernatant during the HeLa and THP-1 assays described above. Then, 50 mL/well of CellTiterGlo (Promega) was added directly to the remaining cells and plates incubated for 10 minutes at room temperature. Assay plates were read for luminescence on an Envision plate reader (Perkin Elmer). To calculate percent cell viability in a sample, luminescence values were normalized to the average of the control DMSO-only treatment wells on the plate, where DMSO-only was set at 100% viability.

C. Human Whole Blood Assay

Human whole blood was collected in sodium heparin and gently mixed. Then 25 mg/mL LPS (Sigma) and 100 ng/mL IFNg (R&D) was added and transferred immediately to a 96-well U bottom plate, 200 mL per well. PF-06840003 was prepared in dimethyl sulfoxide (DMSO) and aliquotted to individual wells to final concentration from 0.01 to 100 µM. The final DMSO concentration was 0.5%. Following overnight incubation at 37° C., a 30 mL aliquot was precipitated with 270 mL acetonitrile/HPLC water (70:30), vortexed vigorously, and centrifuged at 3220×g for 15 minutes at 10° C. An aliquot of the supernatant organic solution was diluted in 0.1% Formic acid and spiked with stable labeled isotopes of kynurenine and tryptophan as internal standards prior to analysis. Kynurenine inhibition was determined by dividing the drug treated internal standard adjusted kynurenine counts by the positive control internal standard adjusted value. The no drug treated sample containing DMSO was used as the positive control. In order to quantify PF-06840002, a calibration standard curve was prepared in untreated (i.e., no drug, LPS, or IFNg) whole blood. The $IC_{50}$ and $IC_{90}$ calculations were conducted in GraphPad Prism version 6.03.

In order to determine compound potency in a human cellular system, human whole blood was collected from 9 subjects. The $IC_{50}$ values were determined from both the nominal spiked PF-06840003 concentrations and the measured PF-06840002 concentrations. Since PF-06840003 is a racemate, the actual active enantiomer, PF-06840002, was measured following overnight incubation with whole blood and agonists. The mean and standard deviation $IC_{50}$ for the nominal PF -06840003 was (4.710±2.408 µM), and the mean and standard deviation $IC_{50}$ for PF -06840002 was (2.505±1.477 µM). The unbound inhibitor $IC_{50}$ and $IC_{90}$ values were computed by applying a conversion for the unbound fraction value in whole blood, 0.419. The unbound PF-06840003 $IC_{50}$ and $IC_{90}$ were determined to be (2.114 and 10.697 µM), respectively. The unbound PF-06840002 IC50 and IC90 were determined to be (1.050 and 5.691 µM), respectively. The human whole blood assay provided a selective assessment of IDO-1 activity in a relevant model. The IC50 determined from samples from 9 donors for PF-06840003 was 4.710±2.408 µM.

D. Results

1. Enzyme Inhibition

Biochemical potency (IC50) was determined for PF-06840003 (racemic mixture) as well as PF-06840002 (active enantiomer), and PF-06840001 (inactive enantiomer). These data are summarized in Table 1. $IC_{50}$ values are listed as the geometric mean with the 95% confidence interval in parentheses. Since the MS assay used in these studies is not described in the literature, biochemical potency was determined in a spectroscopic assay previously described in the literature (Sono & Cady, 1989) to support results from this novel assay. The results from both assays are comparable.

2. Mechanism of Inhibition

Since both PF-06840002 and PF-06840003 are indoles, we investigated the activity of these inhibitors as a function of tryptophan concentration to determine whether the inhibitors were competitive with tryptophan. Using the enzymatic MS assay, inhibition was measured at multiple concentrations of tryptophan substrate from 1 µM to 150 µM as well as multiple inhibitor concentrations (0, 0.023, 0.069, 0.21, 0.625, 1.9, and 5.6 µM). Additionally, the binding affinity of these inhibitors against different redox forms of human IDO1 was investigated.

3. Kinetic Studies

Model comparison using Prism software (GraphPad Software, Inc), gave the best fit to a model for uncompetitive inhibition for the human enzyme studies, and noncompetitive inhibition for the dog enzyme studies.

4. UV Spectroscopic Binding Studies

Figure 2:
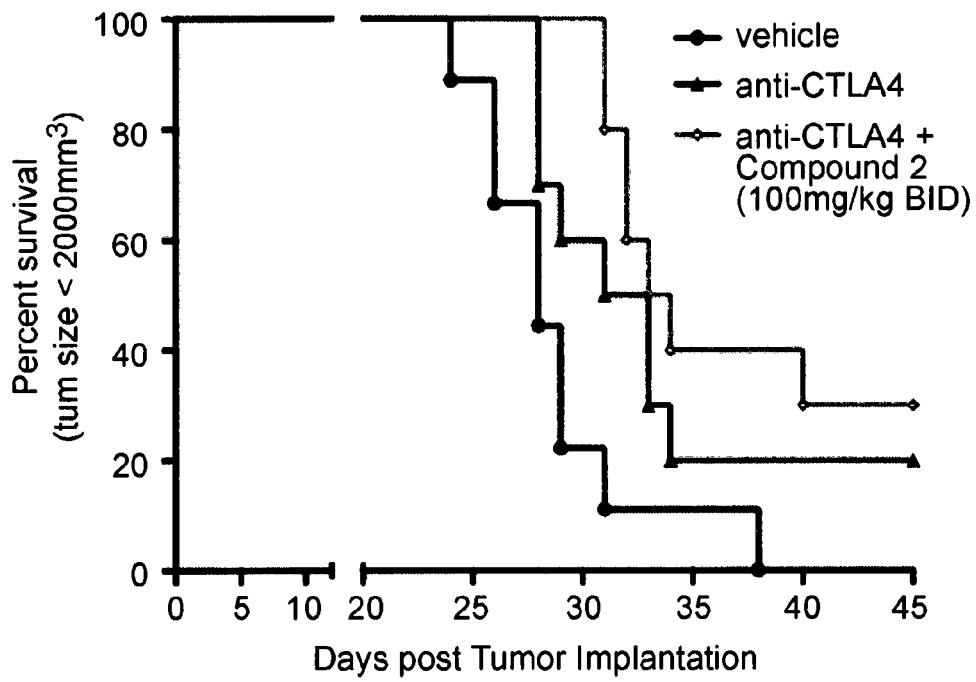
FIG. 2 is a graph showing survival rate in a murine colon cancer model following combination treatment with compound 2 and a murine anti-CTLA4 antibody as compared to vehicle using a tumor size cutoff of 2000 mm$^3$.

Titration of both PF-06840002 and PF-06480003 into multiple redox forms of hIDO1 was performed. Specifically, the compounds were evaluated for the ability to bind both ferric and ferrous forms of hIDO1. Additionally, binding to ferric IDO following depletion of $O_2$, tryptophan was also investigated. Evaluation of the active enantiomer, PF-06840002, was also performed to ensure that the behavior of the investigational compound, PF-06840003, was not altered by the presence of the inactive enantiomer. Data for PF-06840002 were similar to those of PF-06840003. Technical difficulties were encountered for the specific condition where PF-06840003 was titrated into ferric IDO1 plus tryptophan, after oxygen depletion. The magnitude of the peak at 405 nm was erratic. The peak height was not stable, moving both up and down with repeat measurements of the same condition. As a result, compound titration was not possible. Work is ongoing to understand the cause of the variability. This behavior was not seen with the active enantiomer, PF-06840002; therefore, the PF -06840002 result is shown in FIG. 2 and summarized in Table 2.

E. Conclusions

PF-06840003 (racemate) and both enantiomers, PF-06840002 and PF -06840001 were biochemically characterized for the ability to inhibit mouse, dog and human IDO1 enzymatic activity. IC50 values for PF-06840003 were similar for dog and human enzyme forms (0.59 µM vs 0.40 µM, respectively), and showed a 3.8-fold decrease in potency for the mouse enzyme compared to human (1.5 µM vs 0.40 µM). For the active enantiomer, PF-06840002, the IC50 values were comparable for dog and human (0.20 µM vs 0.20 µM, respectively) while the inhibition of the mouse enzyme was 3.7-fold weaker than human (0.73 µM vs 0.20 µM). PF-06840001 showed no inhibition up to 10 µM. In order to better understand the mechanism of inhibition, inhibitory activity of PF-06840002 and PF-06840003 were further investigated using the enzymatic MS assay. Inhibition was measured at several different concentrations of tryptophan substrate as well as various different inhibitor concentrations. For both active compounds, the preferred fit was to a model for uncompetitive inhibition when using the human enzyme and noncompetitive inhibition when using the dog enzyme. In all cases, a mechanism where the compounds were competitive with tryptophan was ruled out. Further work is necessary to determine if the difference in mechanism between human and dog isoforms is real and not an artifact resulting from experimental error or differences in heme loading between the two enzymes. IDO1 is a heme bound protein which can exist in multiple redox forms including the ferric ($Fe^{3+}$) and ferrous ($Fe^{2+}$) forms. Tryptophan is known to bind with significantly higher affinity to the ferrous form than to the ferric form (Sono & Cady, Biochemistry, 29(13): 5392-5399 (1989). Further analysis using a spectrophotometric binding assay showed that PF-06840003 bound weakly to both the ferric and ferrous forms of IDO1 in the presence of oxygen with apparent binding constants of 14 and 22.3 µM, respectively. The peaks in the Soret region of the spectra do not shift upon compound binding indicating that the compound did not perturb heme binding or interact directly with the heme. Under conditions where the oxygen content was depleted, PF-06840003 bound to the ferric form of IDO1 with an apparent binding constant of 0.32 µM. This value is in line with the IC50 value determined kinetically and suggests that the ferric form, without oxygen bound at the heme, is the form of the enzyme that the inhibitor binds to during catalysis. Since tryptophan did not bind this form of the enzyme tightly, a mechanism where PF-06840003 is competitive with tryptophan is excluded, consistent with the kinetic results. To further illustrate this, the apparent inhibitor binding constant of oxygen depleted, ferric IDO1 was determined. PF-06840003 did not behave well in this experiment so PF-06840002 was used. Consistent with a non-competitive mechanism, the IC50 for PF-06840002 was unchanged when tryptophan was added. Therefore, PF-06840003 is a potent, tryptophan non-competitive, non-heme binding inhibitor of IDO1. Similar results were shown for the active enantiomer, PF-06840002, indicating that the behavior of the racemic mixture and the pure enantiomer are comparable.

PF-06840003 inhibits cellular hIDO1 enzyme production resulting in reductions in kynurenine levels in both HeLa cervical carcinoma and monocytic THP-1 cells. This was demonstrated in HeLa and THP-1 cells following IDO1 induction with pro-inflammatory cytokine treatment. The PF-06840003 racemate was less potent in both cell models ($IC_{50}$=1769 nM in HeLa, 1658 nM in THP-1) than the enantiomer PF-06840002 ($IC_{50}$=1047 nM in HeLa, 1112 nM in THP-1), consistent with PF-06840002 characterization as the active enantiomer. The inactive enantiomer, PF-06840001 was much less active in both the HeLa and THP-1 cellular assays ($IC_{50}$=12764 nM and 5844 nM, respectively). Reduction in IDO activity/potency was not due to a reduction in cell viability during these experiments. The preclinical studies described demonstrate that the small molecule inhibitor PF-06840003 inhibits hIDO1 as measured by kynurenine production in two cellular models.

Example II.9: IDO1 Inhibitor PF06840003 Rescues T Cell Proliferation in a T Cell —SKOV3 Co-Culture Assay In order to mimic the physiological consequences of IDO1 expression in the tumor microenvironment on T cell proliferation, assay was designed based on the co-culture of IDO1-expressing tumor cells and T lymphocytes. The SKOV3 human ovarian carcinoma cell line constitutively expresses IDO1.

SKOV3 cells (ATCC) were seeded in IMDM with 10%, 25% or 50% of Human Serum (HS) (Sigma), treated with increasing concentrations of PF-06840003 and then irradiated (10,000 rad). Human peripheral blood mononuclear cells were isolated from buffy coats, purified by density gradient centrifugation on Lymphoprep™ (StemCell), stimulated with CD3/CD28 beads (Invitrogen) and hIL-2 (Novartis) in IMDM with 10%, 25% or 50% of HS, for 15 min and then added to the SKOV3 plates. All samples were done in duplicate in one plate for T cell proliferation measurement and as a single replicate in another plate for tryptophan and kynurenine measurement. After an incubation of 24 h, the tryptophan and kynurenine concentrations in conditioned medium were assessed using LC-MS/MS. $^3$H-thymidine was added to the co-cultures for another 24 h incubation period. Thymidine incorporation was measured using a TopCount counter (Perkin Elmer). Data were fitted and $IC_{50}$ determined by using the Prism™ software (Graph-Pad software Inc.).

Figure 7D:
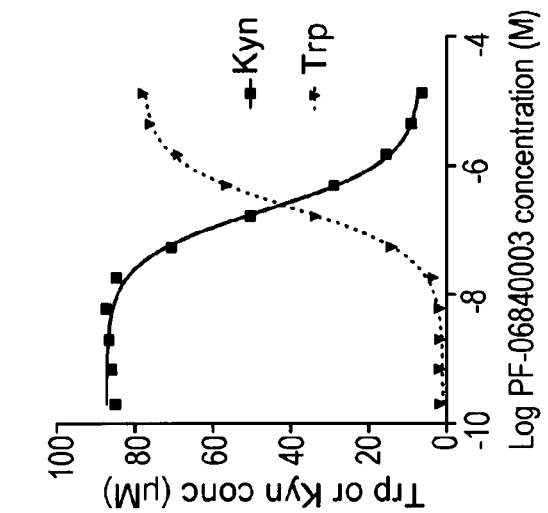
Figure 7E:
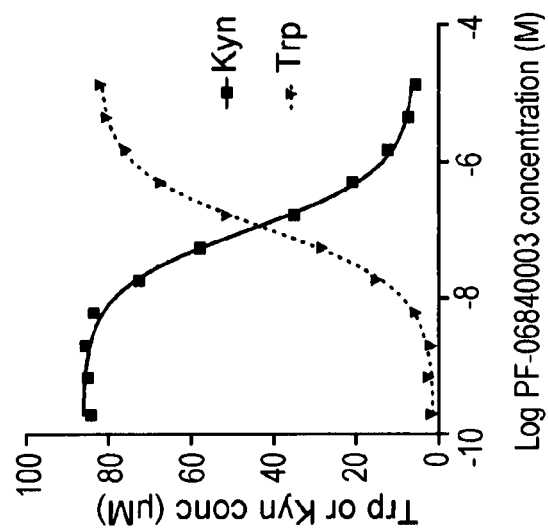
Figure 7F:
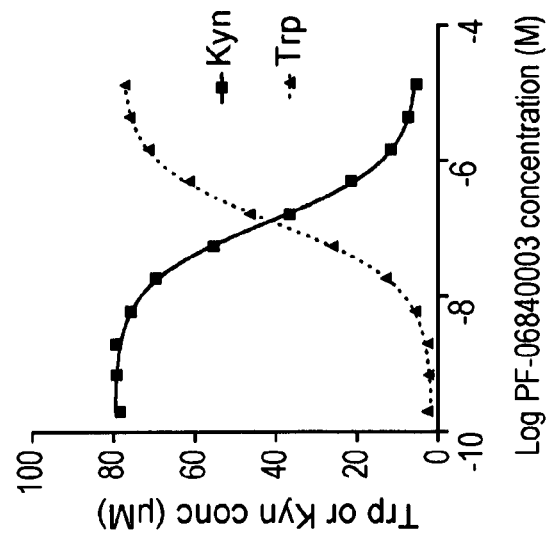
Figure 8B:
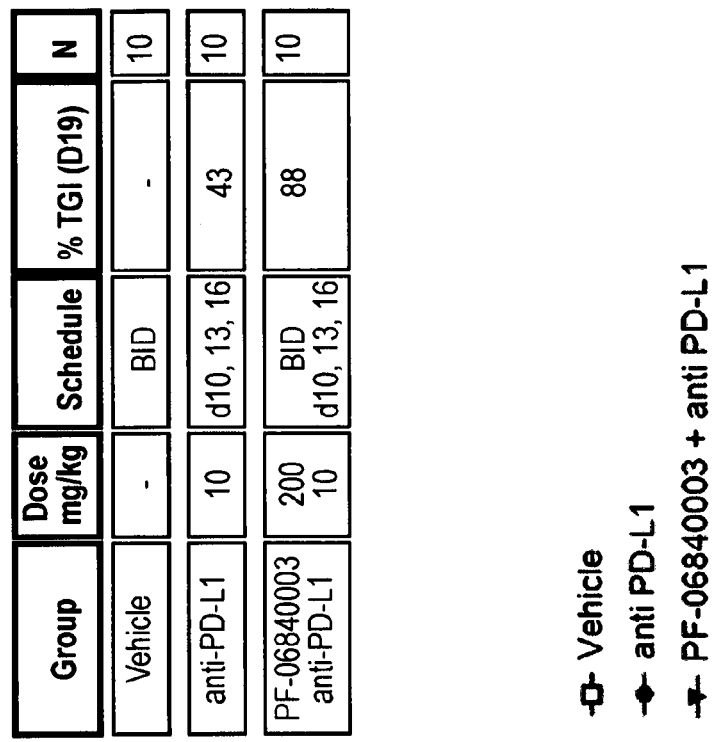
Figure 8A:
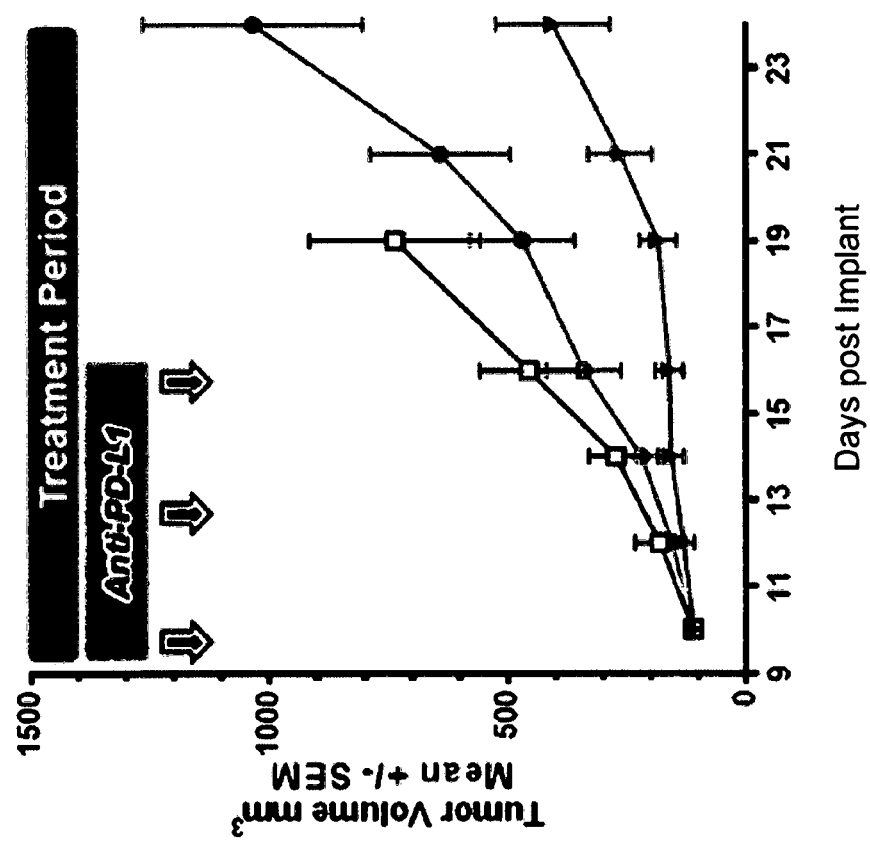
Figure 9A:
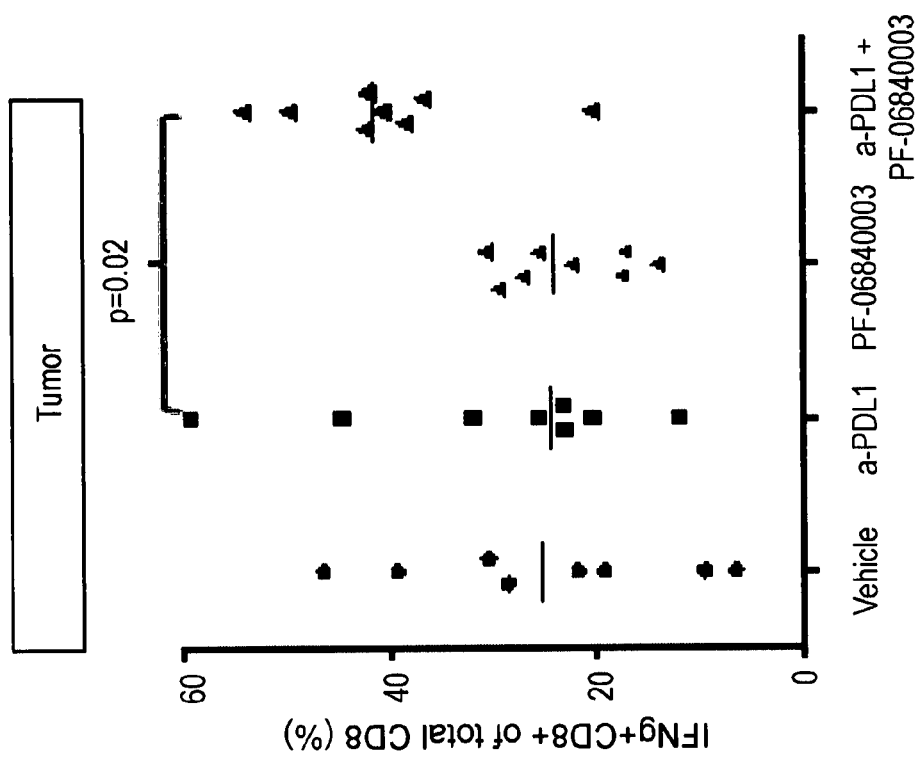
FIGS. 9A-D are scattergrams which show that the combined treatment of the IDO1 inhibitor and anti-PD-L1 specifically causes an increase of activated T-cells in the tumor and not in the periphery (e.g., spleen) as determined by using an intracellular IFN-γ readout in CD4$^+$ and CD8$^+$ T-cells after 3 h incubation in presence of PMA+Ionomycine and Golgi transport inhibitor. The fraction of CD4$^+$IFNγ and CD8$^+$IFNγ$^+$ T-cells in CT26 tumors was increased following combined anti-PD-L1 and IDO1 inhibitor treatment.
Figure 9B:
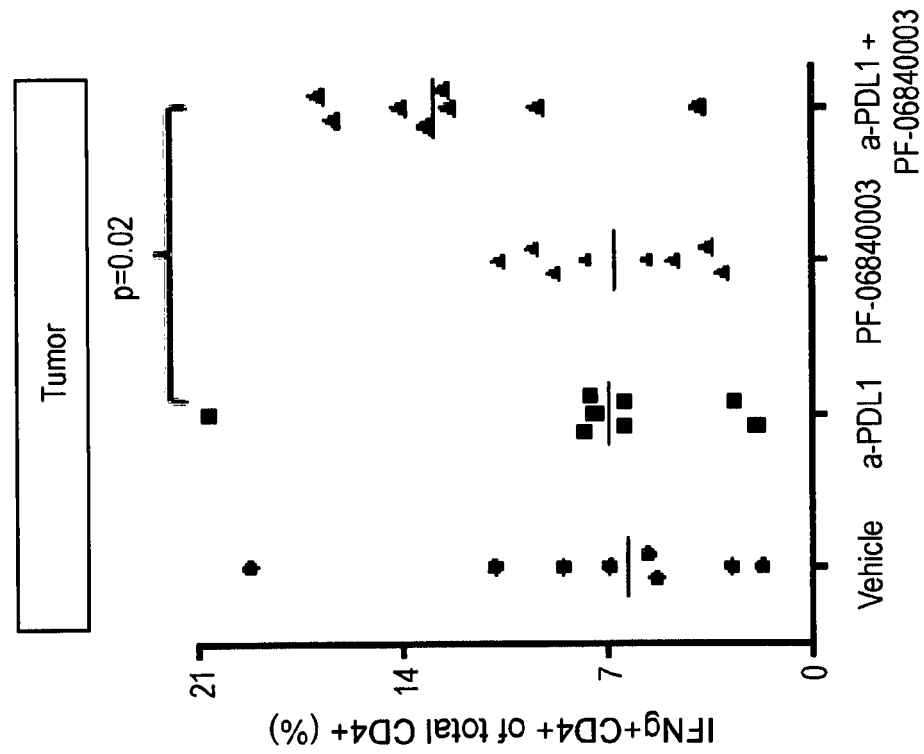
Figure 9D:
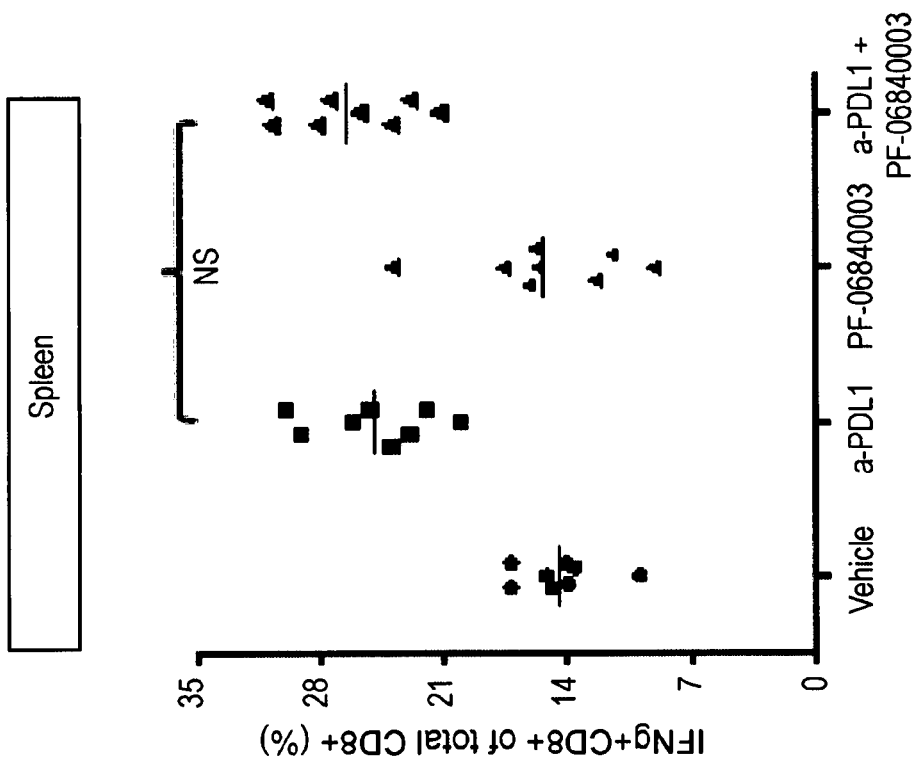
Figure 9C:
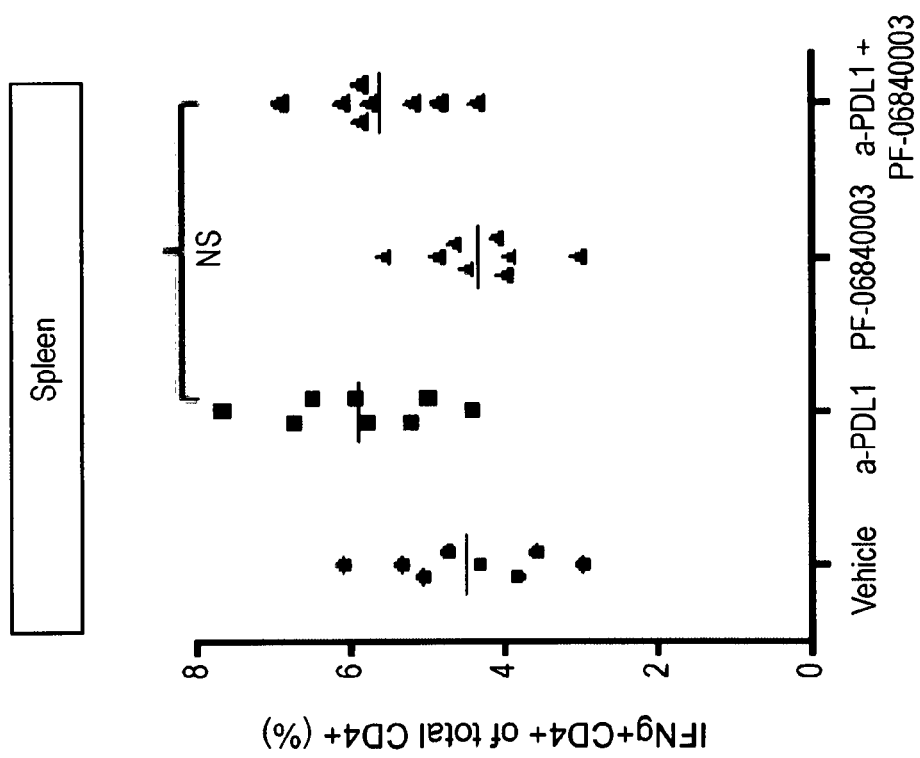

The IDO1 inhibitor racemic 3-(5-fluoro-1H-indol-3-yl)pyrrolidine-2,5-dione effectively rescued IDO1-induced T cell anergy in this assay with an $IC_{50}$ of 74 nM in the presence of 50% serum (FIGS. 7A-7C). The tested racemic compound efficiently inhibited tryptophan to kynurenine conversion by SKOV3 cells (FIGS. 7D-7F) in the same assay. The ability of racemic 3-(5-fluoro-1H-indol-3-yl)pyrrolidine-2,5-dione to rescue T cell proliferation seemed to be serum-independent (with $IC_{50}$ varying from 60 to 74 nM in serum concentrations ranging from 10% to 50%).

Example III.1: In Vivo Efficacy Studies on Inhibition of Tryptophan Degradation in CT26 Tumor Tissue Using Combinations of an IDO Inhibitor Compound and an Anti-CTLA4 Antibody A. IDO Inhibitor Compounds Reduce Kynurenine Concentration in Tumor Induced by an Anti-CTLA4 Antibody.

A further study of the combination of an IDO inhibitor compound provided herein and an anti-CTLA4 antibody [murine monoclonal antibody, anti mCD152 (murine CTL-4), Clone 9H10, available from BioXCell, Catalog #BEO131], were performed on a CT26 syngeneic tumor model of Balb/c mice implanted subcutaneously as described in Part A of Example II.7. In brief, five hundred thousand CT26 colon carcinoma cancer cells were implanted subcutaneously in 7 weeks old Balb/c mice (day 0). Animals were randomized based on tumor size when tumor average was between 100 and 150 mm$^3$ (day 10) into different treatment cohorts (Methocel® methylcellulose, anti-CTLA-4 (60 µg, intraperitoneally (i.p.)), Compound 2 100 mg/kg twice a day (BID)+anti-CTLA-4 (60 µg, i.p.) n=10/group). Methocel® vehicle or 100 mg/kg of Compound 2 was administered orally twice per day (8 hours apart) starting the day of randomization. Anti-CTLA4 (Clone 9 h10, 60 µg/mouse, i.p. in PBS) was administered at day 10, 13 and 16. Compound 2 was resuspended into Methocel® vehicle and sonicated before oral administration to animals using gavage needles. Treatment was administered daily until the end of the study. Tumor volume was measured weekly using a caliper device and calculated with the following formula: Tumor volume=0.5×(length×width$^2$). When the tumor reached a size of 2000 mm$^3$, mice were sacrificed 4 h after Compound 2 administration. The tumor was removed, weighted and frozen on dry ice. Tumors were analyzed by LC/MS-MS for Kynurenine concentration. FIG. 1 shows that the combination of compound 2 and an anti-CTLA4 antibody decreases Kynurenine concentration in tumor.

| Treatment | Kynurenine concentration (ng/g tumor) Average +/− SEM |
|---|---|
| Vehicle Methocel | 1343 +/− 131 |
| Anti-CTLA4 | 2461 +/− 347 |
| Anti-CTLA4 + Compound 2 (100 mg/kg BID) | 851 +/− 175 |

B. In Vivo Efficacy Studies with CT26 Colon Carcinoma Syngeneic Model

Figure 3:
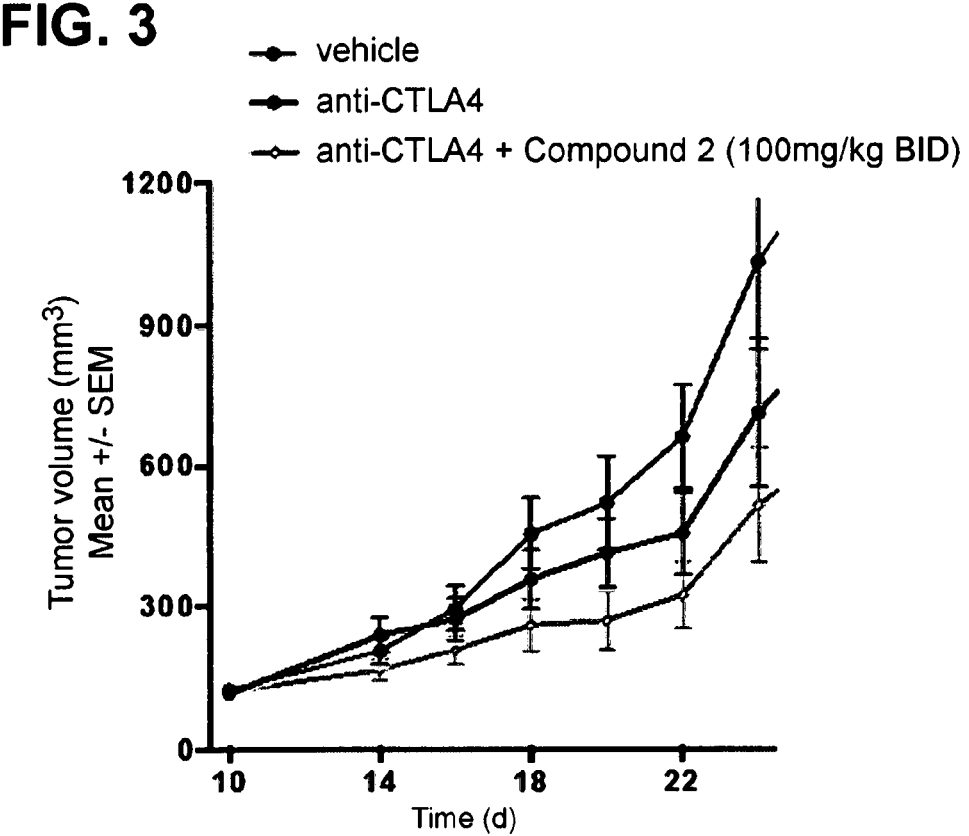
FIG. 3 is a graph showing the tumor growth of CT26 tumors in Balb/c mice receiving Compound 2, a murine anti-CTLA4 antibody, or a combination thereof.

In vivo efficacy studies of the IDO1 inhibitor of Compound 2 were performed on CT26 syngeneic tumor model of Balb/c mice implanted subcutaneously, essentially as described above. Five hundred thousand CT26 colon carcinoma cancer cells were implanted subcutaneously in 7 week old Balb/c mice (day 0). Animals were randomized based on tumor size when tumor average was between 120 and 150 mm$^3$ (day 10) into different treatment cohorts (Methocel, anti-CTLA-4 (60 µg, i.p.), Compound 2 100 mg/kg BID+ anti-CTLA-4 (60 μg, i.p.) n=10/group). Methocel vehicle or 100 mg/kg of Compound 2 was administered orally twice per day (8 hours apart) starting the day of randomization. Anti-CTLA4 (Clone 9 h10, 60 μg/mouse, i.p. in PBS) was administered at day 10, 13 and 16. Compound 2 was resuspended into Methocel vehicle and sonicated before oral administration to animals using gavage needles. Treatment was administered daily until the end of the study. Tumor volume was measured weekly using a caliper device and calculated with the following formula: Tumor volume=0.5× (length×width$^2$). Mice were sacrificed when tumor size reached 2000 mm$^3$. FIGS. 2 and 3 show that the combination of the IDO1 inhibitor and the anti-CTLA4 antibody prolongs survival and inhibits tumor growth (see table below).

| Treatment | Average tumor size at day 24 +/− SEM (mm$^3$) |
|---|---|
| Vehicle | 1033 +/− 185 |
| Anti-CTLA4 | 712 +/− 158 |
| Anti-CTLA4 + Compound 2 100 mg/kg BID | 516 +/− 122 |

Figure 4:
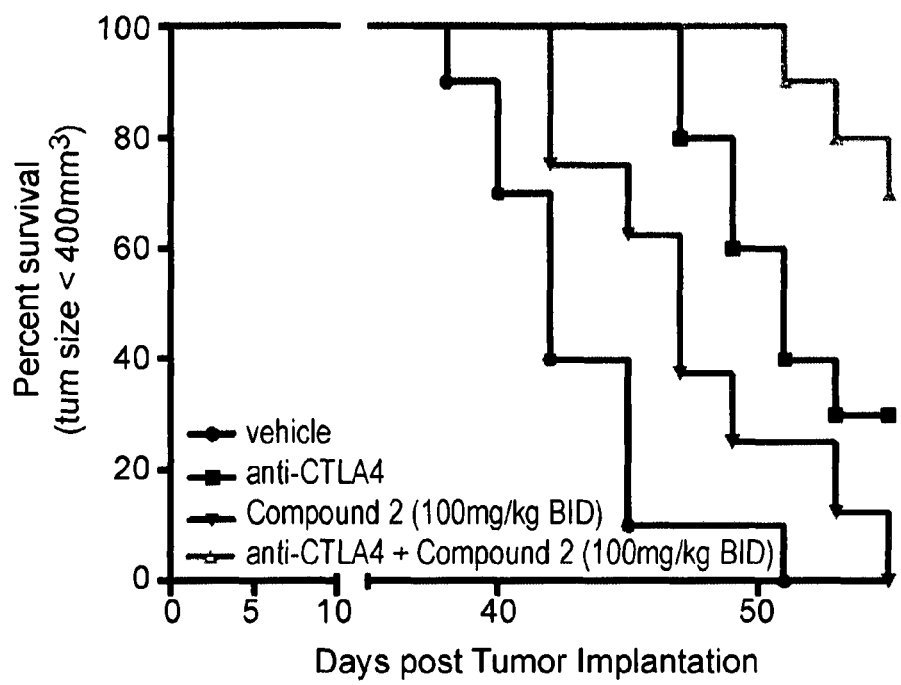
FIG. 4 is a graph showing survival rate in a murine colon cancer model following combination treatment with compound 2 and a murine anti-CTLA4 antibody, using a tumor size cutoff of 400 mm$^3$.
Figure 5A:
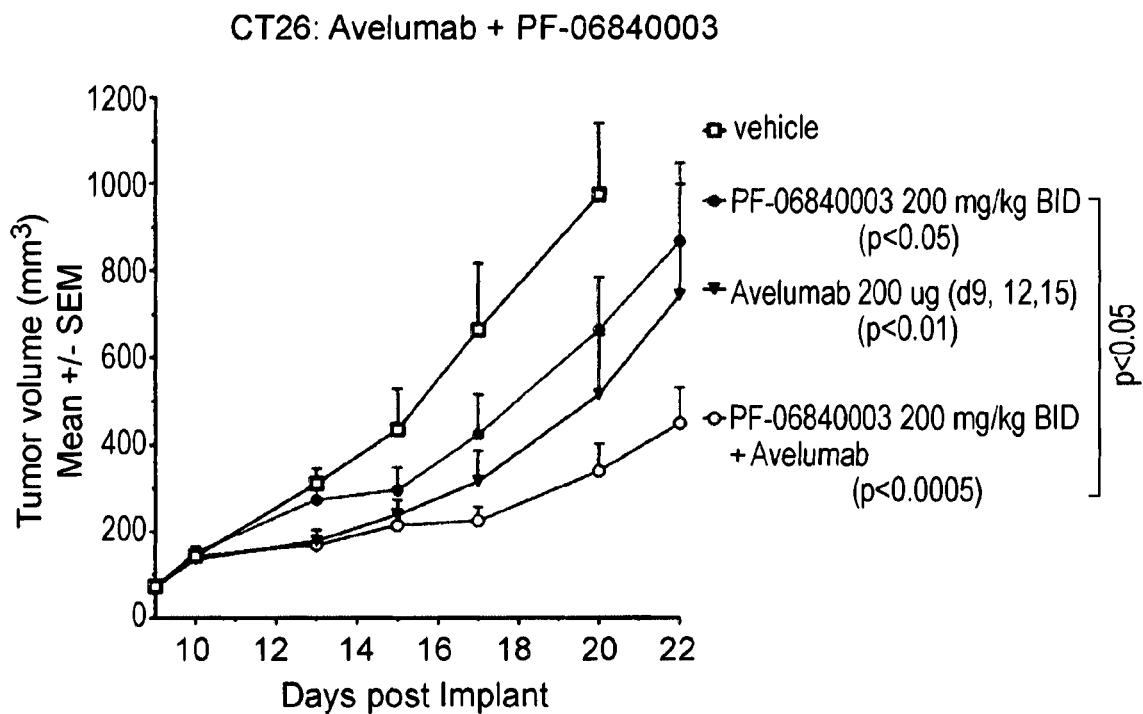
FIGS. 5A-5E show combinatorial anti-tumor effects of an IDO1 inhibitor and an anti-PD-L1 (avelumab) in the sc CT26 syngeneic mouse colon tumor model in Balb/c mice.
Figure 5B:
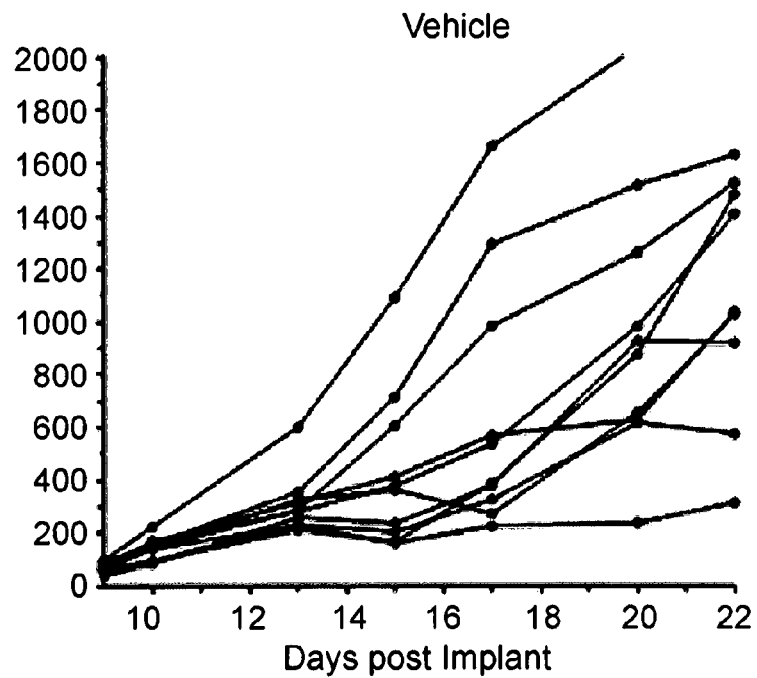
Figure 5C:
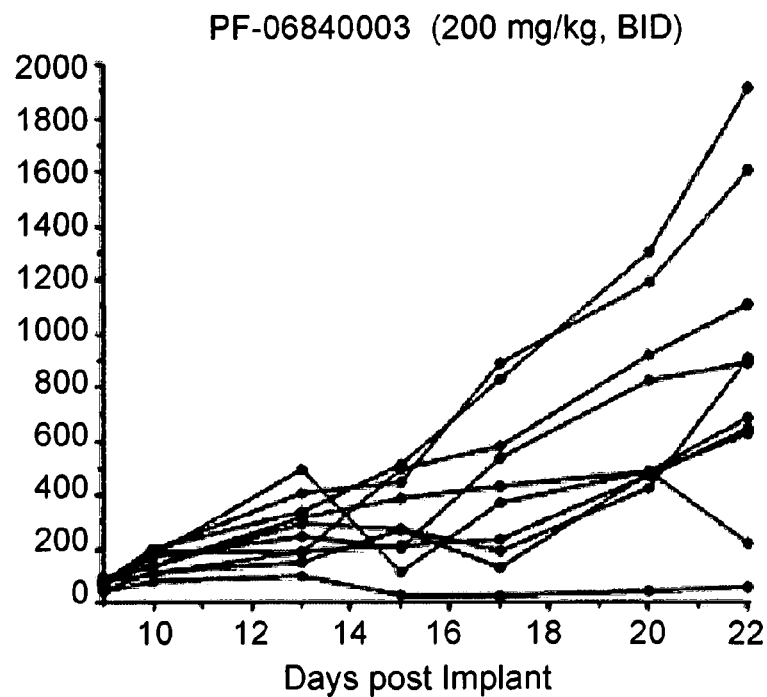
Figure 5D:
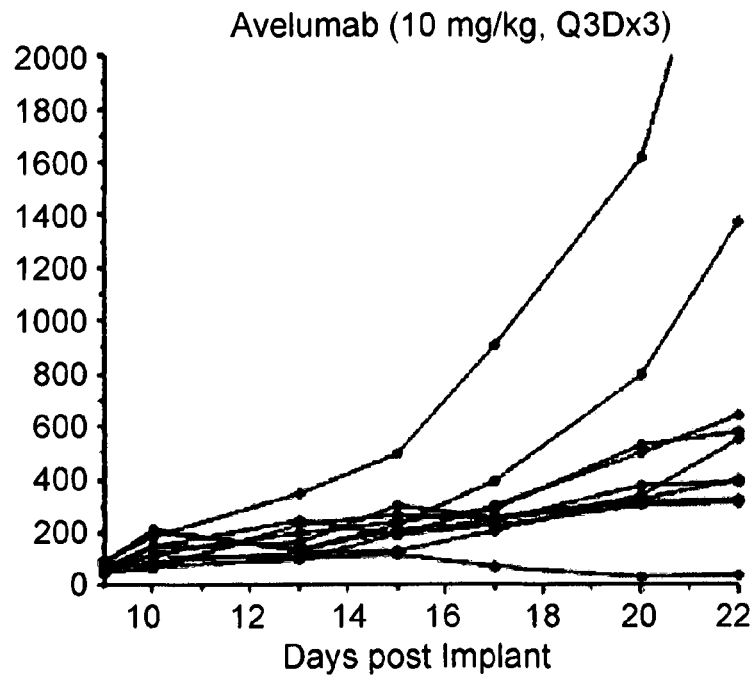
Figure 5E:
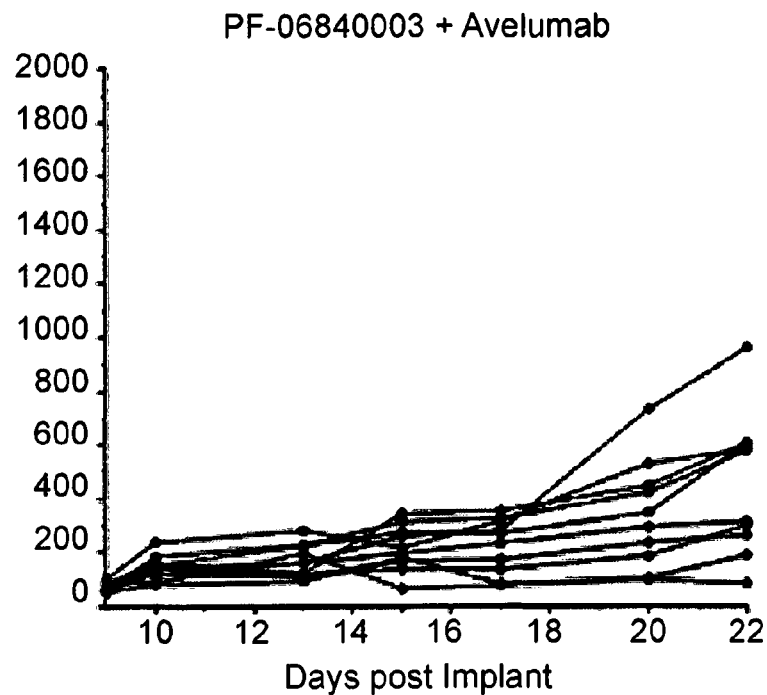
Figure 5F:
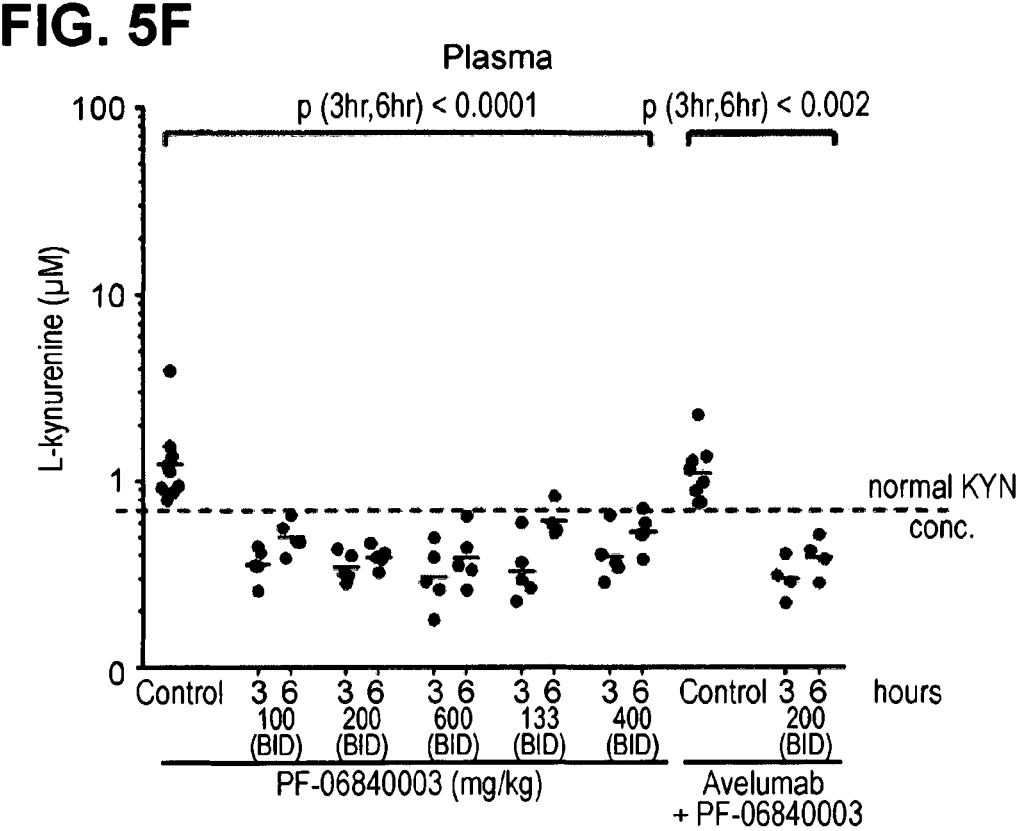
FIGS. 5F-5G show PD modulation in CT26 tumors. The reduction of elevated Kyn levels in tumor tissues serves as a proximal biomarker for racemic 3-(5-fluoro-1H-indol -3-yl)pyrrolidine-2,5-dione mediated IDO inhibition. Effective plasma L-kynurenine modulation was also observed. Plasma Kyn level in non-tumor bearing mice is indicated by the grey dotted line. Statistical analysis was performed with ANCOVA.
Figure 5G:
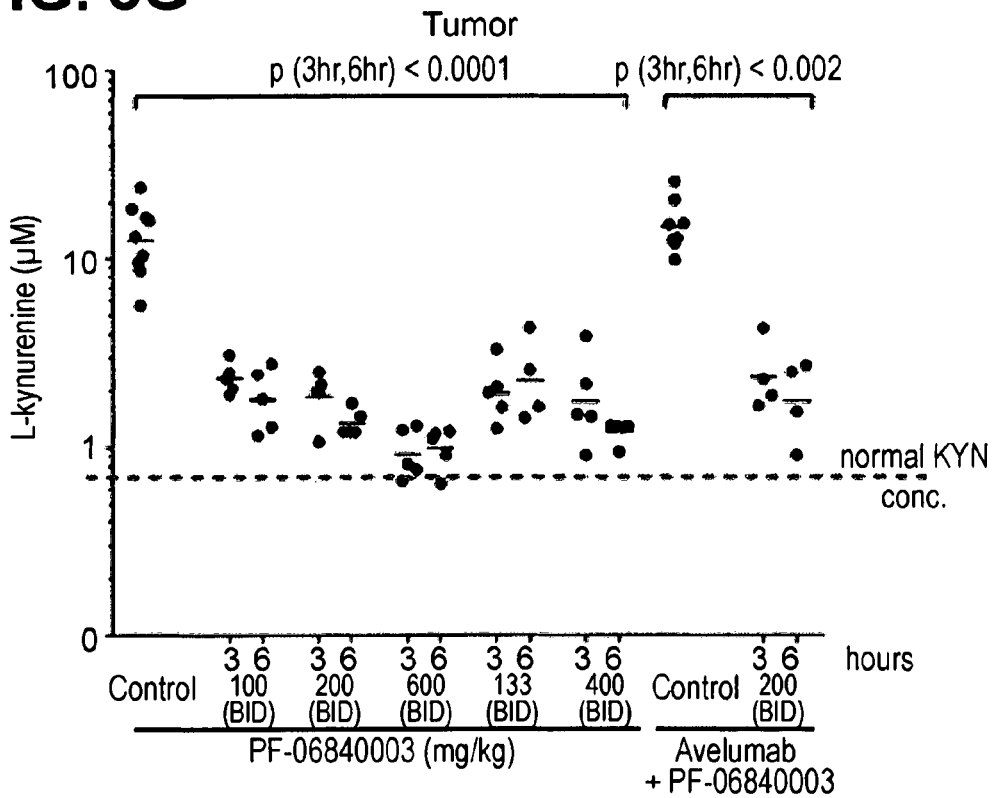
Figure 6A:
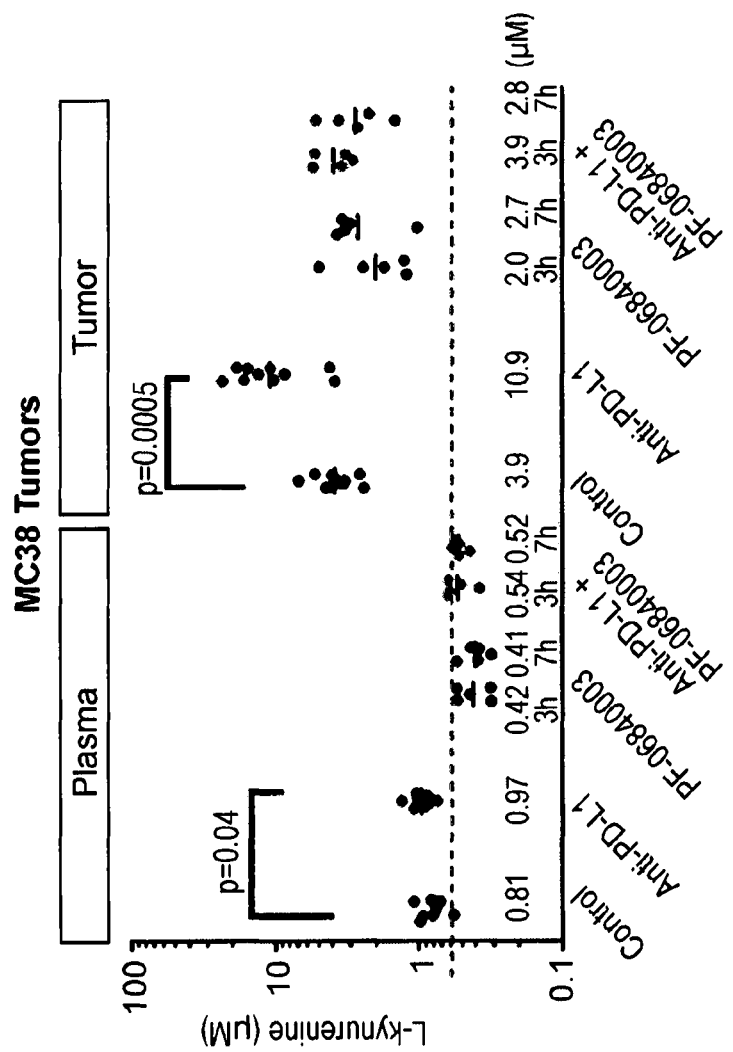
FIG. 6A illustrates activity following anti-PD-L1 treatment elevated IDO1 activity, as demonstrated in heightened Kyn levels, in MC38 tumors are observed linking the immune modulation by anti-PD-L1 mechanistically with IDO1 activity. (n=10; geomean shown; day14 of treatment).
Figure 6B:
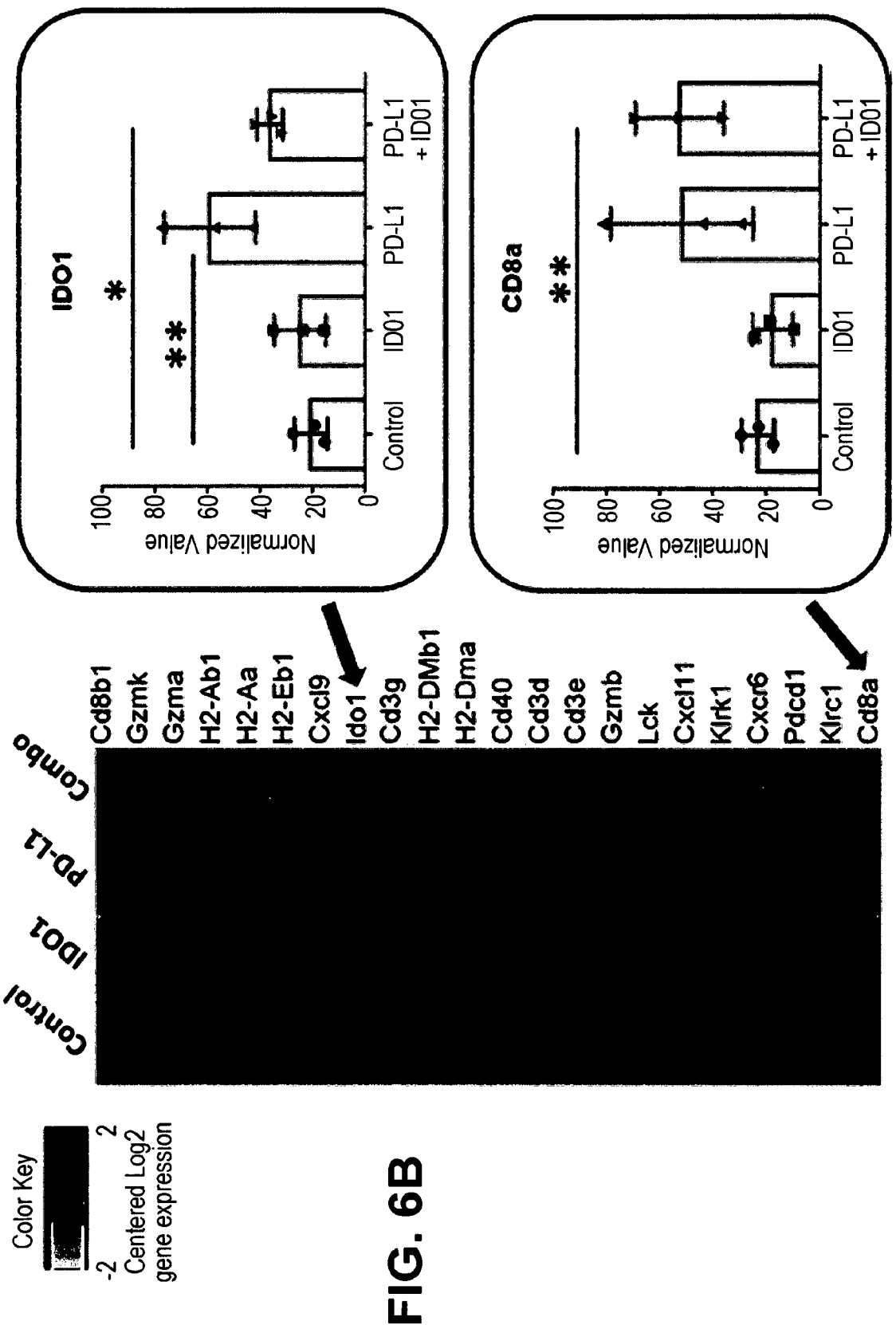
FIG. 6B shows an increase of overall IDO1 expression in MC38 tumors after anti-PD-L1 treatment. Tumors (n=3) were analyzed by nanostring technology on day24 for quantification of gene expression transcript levels with the nCounter mouse Pan cancer immune profiling panel.

Example III.2: In Vivo Efficacy Studies with PancO2 Syngeneic Model Using Combinations of an IDO Inhibitor Compound and an Anti-CTLA4 Antibody In vivo efficacy studies of IDO1 inhibitor were performed on PancO2 syngeneic tumor model of C57/Bl6 mice implanted sub-cutaneously essentially as described in Example II.5. Five million PancO2 pancreas cancer cells were implanted sub-cutaneously to 7 weeks old C57/Bl6 mice (day 0). Animals were randomized based on tumor size, when tumor size was between 30 and 70 mm$^3$ (Day 11) into different treatment cohorts (Methocel® methylcellulose vehicle, Compound 2 100 mg/kg BID, anti-CTLA-4 (200 μg, i.p.), Compound 2 100 mg/kg BID+anti-CTLA-4 (200 μg, i.p.) n=10/group). Methocel vehicle or 100 mg/kg of Compound 2 was administered orally twice per day (8 hours apart) starting the day of randomization. Anti-CTLA4 (Clone 9 h10, 200 μg/mouse, i.p. in PBS) was administered at day 11, 14 and 17. Compound 2 was resuspended into Methocel® vehicle and sonicated before oral administration to animals using gavage needles. Treatment was administered daily until the end of the study. Tumor volume was measured weekly using a caliper device and calculated with the following formula: Tumor volume=0.5×(length× width$^2$). Mice were considered as dead when tumor size reached 400 mm$^3$. The table below and FIG. 4 shows that combination of the IDO1 inhibitor and anti-CTLA4 antibody prolongs survival.

| Treatment | % Survival at Day 55 |
|---|---|
| Vehicle Methocel | 0% |
| Compound 2 100 mg/kg BID | 0% |
| Anti-CTLA4 | 30% |
| Anti-CTLA4 + Compound 2 100 mg/kg BID | 70% |

Example III.3: Anti-PD-L1+IDO1i Show Combination Benefit in CT26 Tumors

This study was conducted in the syngeneic mouse colon cancer model performed essentially as described in Example III.2, substituting an anti-PD-L1 antibody, avelumab, for the anti-CTLA4 antibody described therein in the combination with Compound 1. Avelumab is a fully human anti-PD-L1 IgG1 monoclonal antibody, and thus, is not optimized for mouse.

| GROUP | DOSE mg/kg | SCHEDULE | % TGI (D15) | % TGI (D17) | % TGI (D20) | N |
|---|---|---|---|---|---|---|
| Vehicle | — | BID | — | — | — | 10 |
| Compound 1 | 200 | BID | 38 | 41 | 34 | 10 |
| Avelumab | 10 | d 9, 12, 15 | 54 | 59 | 51 | 10 |
| Compound 1 + Avelumab | 200 10 | BID D 9, 12, 16 | 60 | 74 | 70 | 10 |

This study shows that the combination of Compound 1 and an anti-PD-L1 antibody has a tumor growth inhibition (TGI) of about 70%, as compared to avelumab alone (about 50% TGI) and Compound 1 alone (about 30 to 40% TGI). See, FIG. 5.

In a more recent study, the efficacy of IDO1 inhibitor Compound 1 was tested against s.c. CT26 tumors.

a. Mice, Cell Lines and Abs 7 weeks old female Balb/C mice were purchased from Charles River. CT26 cell line a was obtained from ATCC. CT26 was grown in RPMI supplemented with 10% (vol/vol) FCS, Hepes (10 mM final) and 2% penicilin/streptomycin. Blocking anti-mouse PDL1 antibody for in vivo model was obtained from BioXcell (clone 10F.9G2). APCeFluor780-conjugated anti-mouse CD45 (30F11), FITC-conjugated anti-mouse CD4 (RM4-5), PECy7-conjugated anti-mouse CD8a (53-6.7), APC-conjugated anti-mouse IFN-gamma (XMG1.2) as well as Cell Stimulation Cocktail kit (+protein transport inhibitor) were all obtained from eBiosciences.

B. In Vivo Tumor Treatment

For in vivo experiments, 5×10$^5$ CT26 cells were resuspended in supplemented-free RPMI and injected s.c. (100 μL) using insulin syringes. Mice were randomized and treatment was started when the tumor had an average of 100 to 120 mm$^3$+/−50 mm$^3$. Antibody treatment consisted in 3 i.p. injection with 200 μg anti-mouse PDL1 separated by 3 days. IDO1 inhibitor (Compound 1) was resuspended and sonicated in Methocel vehicle (Colorcon) and mice were treated twice daily (BID) by oral gavage in the morning and evening (100 μL) until the end of the model.

C. Ex-Vivo Analysis of TIL and Splenocytes

Mice were sacrificed the day after the last antibody treatment (7 days after start of the treatment) and tumors and spleen were excised from animals. Spleen were crushed on MACS Smart Strainer 70 and red blood cells were lysed in RBC lysis buffer (Sigma). Splenocytes were washed in PBS and counted. Tumors were enzymatically digested in gentleMACS C tubes using gentlemACS Dissociator and Tumor Digestion Kit (mouse) from Miltenyi following the manufacturer instructions. After dissociation, TIL were enriched by gradient centrifugation on Lymphoprep. Enriched TIL were then washed in PBS and counted. Cells were treated 3 h in presence of PMA, Ionomycin, Brefeldin A and Monensin according to the manufacturer's protocol (Cell Stimulation Cocktail kit from eBioscience). Cells were placed overnight at 4° C. The next day, Live Splenocytes and enriched TIL were stained using Livid dye (Life Technologies). Fc receptors were blocked by incubation with Fc Block (eBiosciences) before the second staining with a-CD45, a-CD4 and a-CD8. Cells were washed and incubated overnight in IC fixation buffer (eBiosciences). Finally, cells were stained with a-IFN-gamma resuspended in Perm Buffer (eBiosciences). After washing, flow cytometry was performed on a MACSQuant device and data were analysed using FlowJo.

D. Statistics

Tumor growth data were analyzed using ANCOVA.

III.4—Immune Modulation and Anti-Tumor Efficacy for IDO Inhibitor in Combination with Anti-PD-L1 Antibody and 4-1BB B16-F10 cells were obtained from the ATCC and grown following instructions on ATCC's website. $2 \times 10^5$ cells were implanted in 100 ml PBS sc in the right flank of female C57BL/6J (Jackson labs) mice. Mice (n=20) were randomized into treatment groups and treatment initiated on day 9 after implant at a mean tumor size of 60 mm3. Antibody treatments were given as i.p. injection on day 9, 12, 15 and 18. anti-PD-L1 antibody (clone 10F.9G2; rat IgG2b) was purchased from BioxCell. anti-4-1BB antibody (MAB9371; rat IgG1—murinized) was purchased from R&D systems. IDO1 inhibitor (PF-06840003) was resuspended and sonicated in Methocel vehicle (0.5% methyl-cellulose, Colorcon) and mice were continuously treated twice daily (BID, 8/16 h apart) by oral gavage. All animal experimentation was approved in advance by and executed following Pfizer's IACUC.

Figure 11A:
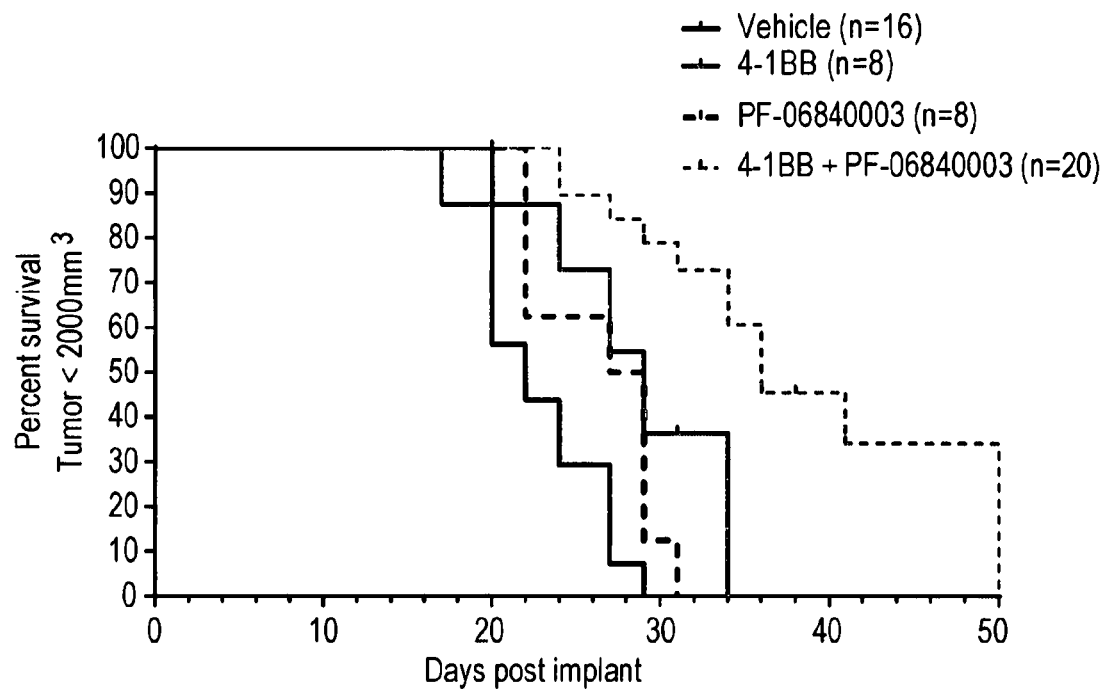
FIGS. 11A-11B are survival graphs which show the increased median survival rate for combination with the IDO1 inhibitor, an anti-PD-L1 antibody and a 4-1BB inhibitor, as compared to anti-4-1BB and anti-PD-L1 treatment.
Figure 11B:
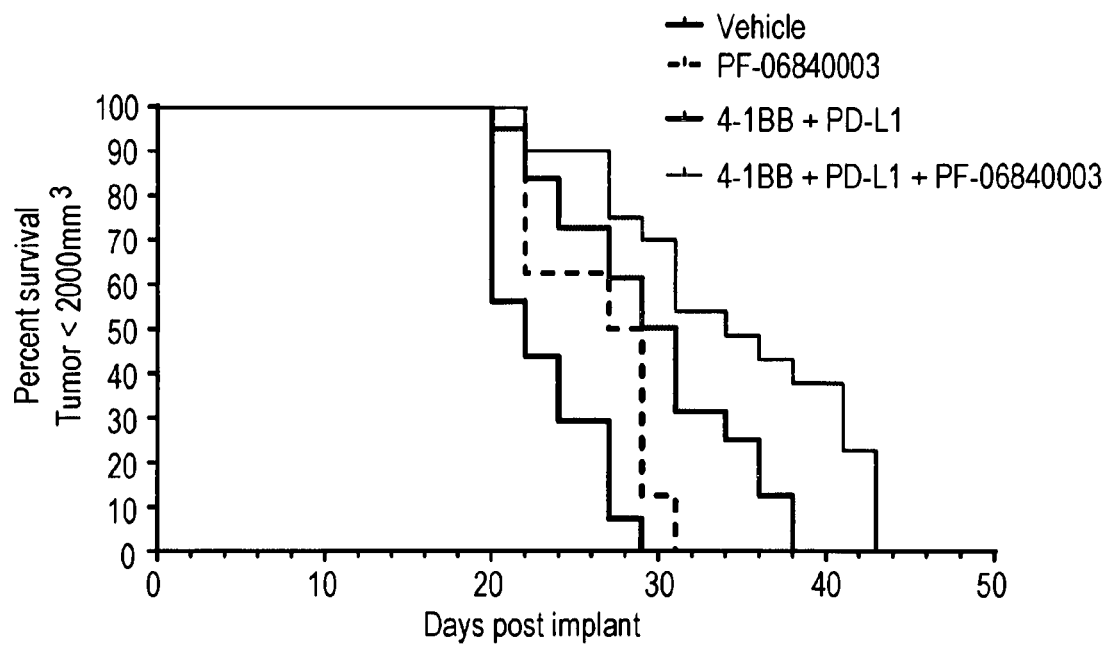

<0.00005). FIG. 11 shows individual animal results. FIG. 12 illustrates median survival was improved with continuous IDO inhibition.

A significant tumor growth inhibition (day 17) and survival benefit (survival cutoff set at tumor size <2000 mm$^3$) benefit of anti-4-1BB antibody+PF-06840003 (600 mg/kg, BID) treatment vs. anti-4-1BB Ab (p<0.02) or PF-06840003 monotherapy in the low immunogenic, subcutaneous, syngeneic melanoma mouse tumor model B16-F10.

In addition, a strong, significant TGI and survival benefit was found by combining IDO1 inhibition via PF-06840003 with the combination anti-4-1BB+anti-PD-L1.

Sequence Listing Free Text

The following information is provided for sequences containing free text under numeric identifier <223>.

| SEQ ID NO: (containing free text) | Free text under <223> |
|---|---|
| 1 | <223> anti-PD-L1 antibody heavy chain |
| 2 | <223> anti-PD-L1 antibody heavy chain |

All patent documents and publications cited in this specification are incorporated herein by reference, as are U.S. Provisional Patent Application No. 62/231,122, filed Apr. 13, 2016, U.S. Provisional Patent Application No. 62/161,654, filed May 14, 2015, and the Sequence Listing. While the invention has been described with reference to particular embodiments, it will be appreciated that modifications can

| Group | Dose mg/kg | Schedule | % TGI (D17) | % TGI (D20) | P-value vs. Control (D17) | P-value vs. Control (D20) | P-value vs. 4-1BB + PD-L1 (D17) | N |
|---|---|---|---|---|---|---|---|---|
| Control | — | BID | — | — | — | — | | 16 |
| PF-06840003 | 600 | BID | 32 | 49 | 0.12 | 0.04 | | 8 |
| anti- 4-1BB | 1 | d9, 12, 15, 18 | 29 | 46 | 0.13 | 0.07 | | 8 |
| anti- 4-1BB PF-06840003 | 1 600 | d9, 12, 15, 18 BID | 66 | 81 | <0.00005 | <0.00005 | 0.05 | 19 |
| anti- 4-1BB anti- PD-L1 | 1 10 | d9, 12, 15, 18 | 50 | 68 | 0.003 | 0.0001 | — | 18 |
| anti- 4-1BB anti- PD-L1 PF-06840003 | 1 10 600 | d9, 12, 15, 18 d9, 12, 15, 18 BID | 73 | 80 | <0.00005 | <0.00005 | 0.007 | 20 |

Figure 10:
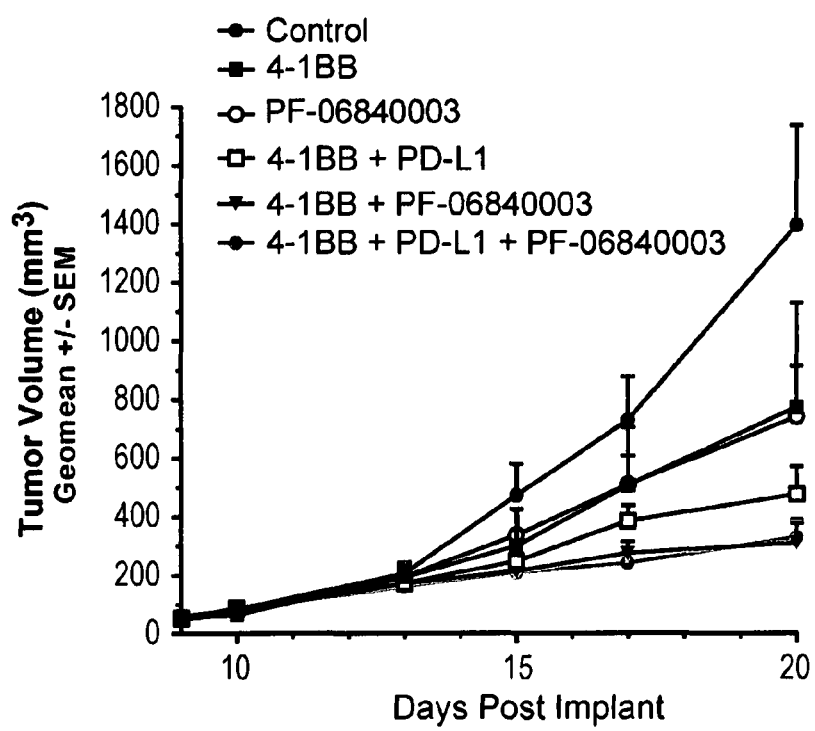
FIG. 10 is a graph showing a combination benefit with the tested IDO1 inhibitor, coadministered with an anti-PD-L1 antibody and a 4-1BB inhibitor, as compared to anti-4-1BB and anti-PD-L1 treatment.

The results shown in FIG. 10 show that anti-4-1BB+anti-PD-L1 antibody+compound 1 is more efficacious than the combination of anti-4-1BB+anti-PD-L1 treatment (p value be made without departing from the spirit of the invention. Such modifications are intended to fall within the scope of the appended claims.

The invention claimed is:

1. A combination regimen useful in cancer treatment comprising the co-administration to a subject in need thereof of (a) at least one indoleamine 2,3-dioxygenase 1 (IDO1) inhibitor, (b) at least one second active component which is an immunomodulatory agent selected from an anti-PD-1 or anti-PD-L1 antibody, and (c) at least a third active component which is an anti-4-1BB antibody, wherein the IDO1 inhibitor is a racemic 3-(5-fluoro -1H-indol-3-yl) pyrrolidine-2,5-dione, the (R)- enantiomer thereof, the (S)-enantiomer thereof, or a mixture thereof.

2. The combination regimen according to claim 1, wherein the IDO1 inhibitor and the anti-PD-1 or anti-PD-L1 antibody are administered to the subject substantially simultaneously.

3. The combination regimen according to claim 1, wherein the IDO1 inhibitor and the anti-PD-1 or anti-PD-L1 antibody are delivered sequentially.

4. The combination regimen according to claim 1, wherein the IDO1 inhibitor and the anti-PD-1 or anti-PD-L1 antibody are delivered via different routes.

5. The combination regimen according to claim 1, wherein the IDO1 inhibitor is administered to the subject orally.

6. The combination regimen according to claim 1, wherein the anti-PD-1 or anti-PD-L1 is administered to the subject via injection.

7. The combination regimen according to claim 1, wherein the IDO1 inhibitor is selected from one or more of 3-(5-fluoro -1H-indol-3-yl)pyrrolidine-2,5-dione in free base form, 3-(5-fluoro-1H-indol-3-yl)pyrrolidine-2,5-dione racemate, an (S)-enantiomer of 3-(5-fluoro-1H-indol-3-yl)pyrrolidine-2,5-dione, or an (R)-enantiomer of 3-(5-fluoro-1H-indol-3-yl)pyrrolidine-2,5-dione.

8. The combination regimen according to claim 7, wherein the 3-(5-fluoro-1H-indol-3-yl)pyrrolidine-2,5-dione racemate is used in the combination, said racemate comprising about 50% (R)- and (S)-enantiomers.

9. The combination regimen according to claim 7, wherein a mixture of (R)- and (S)-enantiomers of 3-(5-fluoro-1H-indol-3-yl)pyrrolidine-2,5-dione are used in the combination.

10. The combination regimen according to claim 9, wherein greater than 50% of the (R)-enantiomer is used.

11. The combination regimen according to claim 9, wherein the mixture of (R) and (S) enantiomers comprises at least 95% to 100% of the (R)-enantiomer.

12. The combination according to claim 1, wherein the cancer is selected from malignant melanoma, acute myelogenous leukemia, pancreatic, colorectal, lung, prostate, cervical, brain, liver, head and neck, endometrial, ovarian cancers or breast cancer.

13. The combination regimen according to claim 1, wherein the subject has a chronic viral infection associated with oncogenesis.

14. The combination regimen according to claim 1, wherein the cancer is breast cancer.

15. The combination regimen according to claim 1, wherein the anti-PD-L1 antibody is avelumab.

16. The combination regimen according to claim 1 which comprises co-administration of a further active component which is an immunomodulatory agent selected from an anti-CTLA4 antibody, an anti-OX-40 antibody, an anti-cancer vaccine, an P-cadherin LP-Dual-Affinity Re-Targeting protein, a TDO inhibitor, a signal modulating inhibitor, an antibody-drug conjugate (ADC), ibrutinib or a chemotherapeutic.

17. The combination regimen according to claim 16, wherein the immunomodulatory agent is an anti-CTLA4 antibody.

18. The combination regimen according to claim 17, wherein the anti-CTLA4 antibody is ipilimumab or tremelimumab.

19. The combination regimen according to claim 16, wherein the further active component is the anti-cancer vaccine.

20. The combination regimen according to claim 16, wherein the further active component is the signal modulating inhibitor, wherein the signal modulating inhibitor is selected from a Pi3K/mTOR inhibitor, a Pi3K-alpha selective inhibitor, an MEK inhibitor, an enhancer of zeste homolog 2 (EZH2) inhibitor, an epidermal growth factor receptor (EGFR) inhibitor, a vascular endothelial growth factor (VEGF) inhibitor, or a selective inhibitor of the cyclin-dependent kinases CDK4 and CDK6.

21. The combination regimen according to claim 20, wherein the signal modualting inhibitor is the Pi3k/mTOR inhibitor which is gedatolisib.

22. The combination regimen according to claim 20, wherein the signal modulating inhibitor is a Pi3K-alpha selective inhibitor.

23. The combination regimen according to claim 20, wherein the signal modulating inhibitor is the selective inhibitor of the cyclin-dependent kinases CDK4 and CDK6, which is palbociclib.

24. The combination regimen according to claim 16, wherein the further active component is a chemotherapeutic which is an alkylating agent.

25. The combination regimen according to claim 24, wherein the chemotherapeutic is temozolomide.

26. The combination regimen according to claim 24, wherein the chemotherapeutic is docetaxel.

* * * * *

SEQUENCE LISTING

<160> NUMBER OF SEQ ID NOS: 2

<210> SEQ ID NO 1
<211> LENGTH: 450
<212> TYPE: PRT
<213> ORGANISM: Artificial sequence
<220> FEATURE:
<223> OTHER INFORMATION: anti-PD-L1 antibody heavy chain

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                    355                 360                 365
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 216
<212> TYPE: PRT
<213> ORGANISM: Artificial sequence
<220> FEATURE:
<223> OTHER INFORMATION: anti-PD-L1 antibody light chain

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```